United States Patent
Helgesen et al.

(10) Patent No.: US 11,983,790 B2
(45) Date of Patent: May 14, 2024

(54) MULTIPROCESSOR PIPELINE ARCHITECTURE

(71) Applicant: Pacific Biosciences of California, Inc., Menlo Park, CA (US)

(72) Inventors: Scott E. Helgesen, Palo Alto, CA (US); Marco Milletti, Sunnyvale, CA (US); Mark T. Lakata, Mountain View, CA (US); James N. LaBrenz, San Francisco, CA (US)

(73) Assignee: Pacific Biosciences of California, Inc., Menlo Park, CA (US)

( * ) Notice: Subject to any disclaimer, the term of this patent is extended or adjusted under 35 U.S.C. 154(b) by 1019 days.

(21) Appl. No.: 15/147,835

(22) Filed: May 5, 2016

(65) Prior Publication Data
US 2016/0328358 A1 Nov. 10, 2016

Related U.S. Application Data

(60) Provisional application No. 62/260,995, filed on Nov. 30, 2015, provisional application No. 62/158,078, filed on May 7, 2015.

(51) Int. Cl.
 G06T 1/20 (2006.01)
 C12Q 1/6869 (2018.01)
 (Continued)

(52) U.S. Cl.
 CPC .............. G06T 1/20 (2013.01); C12Q 1/6869 (2013.01); G16B 30/00 (2019.02); G16B 50/30 (2019.02); G06T 2200/28 (2013.01)

(58) Field of Classification Search
 None
 See application file for complete search history.

(56) References Cited

U.S. PATENT DOCUMENTS

| 4,645,523 A | 2/1987 | Howard et al. |
| 4,818,710 A | 4/1989 | Sutherland et al. |

(Continued)

FOREIGN PATENT DOCUMENTS

| EP | 1229133 A2 | 8/2002 |
| EP | 1105529 B1 | 11/2005 |

(Continued)

OTHER PUBLICATIONS

Alachiotis, N., Berger, S. A. & Stamatakis, A. Efficient PC-FPGA communication over Gigabit Ethernet. in IEEE International Conference on Computer and Information Technology 1727-1734 (IEEE, 2010).*

(Continued)

*Primary Examiner* — Soren Harward
(74) *Attorney, Agent, or Firm* — Morgan, Lewis & Bockius LLP

(57) ABSTRACT

Exemplary embodiments for a multiprocessor pipeline architecture that converts signals from sequencing sample acquisition into sequence data, comprising: a custom coprocessor card configured to directly receive a stream of serialized sensor data generated by an image sensor, wherein the sensor data represents frame-by-frame intensity values for pixels comprising the image sensor, wherein the image sensor captures images of light emitted from a plurality of reaction cells of a removable integrated sequencing chip; a first coprocessor that continually receives the stream of serialized sensor data and transposes the frame-by-frame intensity values into reaction cell chunks, each of the reaction cell chunks representing movie data of the pixel intensity values of a corresponding reaction cell across the frames over a predetermined time window; a buffer that repeatedly receives the reaction cell chunks and stores in contiguous memory locations the reaction cell chunks for each respec- (Continued)

tive reaction cell over a larger predetermined time window to create larger reaction cell chunks; and a plurality of second coprocessors that retrieve the larger reaction cell chunks from the buffer and convert, in parallel, the pixel intensity values into base-by-base sequence data even as additional reaction cell chunks are received by the buffer, such that the second coprocessors begin raw base calling before all the sensor data for the sequencing sample acquisition is obtained. Aspects of the invention include methods for base calling using single instruction multiple data vector processing units.

21 Claims, 9 Drawing Sheets

(51) Int. Cl.
  *G16B 30/00* (2019.01)
  *G16B 50/30* (2019.01)

(56) References Cited

U.S. PATENT DOCUMENTS

| | | |
|---|---|---|
| 5,082,629 A | 1/1992 | Burgess, Jr. et al. |
| 5,094,517 A | 3/1992 | Franke |
| 5,135,876 A | 8/1992 | Andrade et al. |
| 5,157,262 A | 10/1992 | Marsoner et al. |
| 5,159,661 A | 10/1992 | Ovshinsky et al. |
| 5,173,747 A | 12/1992 | Boiarski et al. |
| 5,192,502 A | 3/1993 | Attridge et al. |
| 5,233,673 A | 8/1993 | Vali et al. |
| 5,239,178 A | 8/1993 | Derndinger et al. |
| 5,408,539 A | 4/1995 | Finlay et al. |
| 5,439,647 A | 8/1995 | Saini |
| 5,446,534 A | 8/1995 | Goldman |
| 5,470,710 A | 11/1995 | Weiss et al. |
| 5,545,531 A | 8/1996 | Rava et al. |
| 5,578,832 A | 11/1996 | Trulson et al. |
| 5,605,662 A | 2/1997 | Heller et al. |
| 5,631,734 A | 5/1997 | Stern et al. |
| 5,677,196 A | 10/1997 | Herron et al. |
| 5,695,934 A | 12/1997 | Brenner |
| 5,744,305 A | 4/1998 | Fodor et al. |
| 5,774,305 A | 6/1998 | Boutaghou |
| 5,812,709 A | 9/1998 | Arai et al. |
| 5,821,058 A | 10/1998 | Smith et al. |
| 5,832,165 A | 11/1998 | Reichert et al. |
| 5,867,266 A | 2/1999 | Craighead et al. |
| 5,919,712 A | 7/1999 | Herron et al. |
| 6,002,520 A | 12/1999 | Hoch et al. |
| 6,051,380 A | 4/2000 | Sosnowski et al. |
| 6,071,748 A | 6/2000 | Modlin et al. |
| 6,192,168 B1 | 2/2001 | Feldstein et al. |
| 6,198,869 B1 | 3/2001 | Kraus et al. |
| 6,210,896 B1 | 4/2001 | Chan |
| 6,236,945 B1 | 5/2001 | Simpson et al. |
| 6,263,286 B1 | 7/2001 | Gilmanshin et al. |
| 6,325,977 B1 | 12/2001 | Theil |
| 6,331,441 B1 | 12/2001 | Balch et al. |
| 6,384,912 B2 | 5/2002 | Kraus et al. |
| 6,388,788 B1 | 5/2002 | Harris et al. |
| 6,437,345 B1 | 8/2002 | Bruno-Raimondi et al. |
| 6,438,279 B1 | 8/2002 | Craighead et al. |
| 6,483,096 B1 | 11/2002 | Kunz et al. |
| 6,545,758 B1 | 4/2003 | Sandstrom |
| 6,573,089 B1 | 6/2003 | Vann |
| 6,603,537 B1 | 8/2003 | Dietz et al. |
| 6,611,634 B2 | 8/2003 | Herron et al. |
| 6,633,659 B1 | 10/2003 | Zhou |
| 6,690,002 B2 | 2/2004 | Kuroda et al. |
| 6,692,697 B1 | 2/2004 | Melendez |
| 6,699,655 B2 | 3/2004 | Nikiforov et al. |
| 6,784,982 B1 | 8/2004 | Blumenfeld et al. |
| 6,800,860 B2 | 10/2004 | Dietz et al. |
| 6,818,395 B1 | 11/2004 | Quake et al. |
| 6,867,851 B2 | 3/2005 | Blumenfeld et al. |
| 6,917,726 B2 | 7/2005 | Levene et al. |
| 6,919,211 B1 | 7/2005 | Fodor et al. |
| 6,979,830 B2 | 12/2005 | Dietz et al. |
| 6,982,146 B1 | 1/2006 | Schneider et al. |
| 6,987,613 B2 | 1/2006 | Pocius et al. |
| 7,013,054 B2 | 3/2006 | Levene et al. |
| 7,022,515 B2 | 4/2006 | Herron et al. |
| 7,056,661 B2 | 6/2006 | Korlach et al. |
| 7,057,832 B2 | 6/2006 | Wu et al. |
| 7,075,695 B2 | 7/2006 | Gronbach |
| 7,081,954 B2 | 7/2006 | Sandstrom |
| 7,083,914 B2 | 8/2006 | Seul et al. |
| 7,130,041 B2 | 10/2006 | Bouzid et al. |
| 7,135,667 B2 | 11/2006 | Oldham et al. |
| 7,139,074 B2 | 11/2006 | Reel |
| 7,145,645 B2 | 12/2006 | Blumenfeld et al. |
| 7,150,997 B2 | 12/2006 | Kovacs |
| 7,170,050 B2 | 1/2007 | Turner et al. |
| 7,175,811 B2 | 2/2007 | Bach et al. |
| 7,181,122 B1 | 2/2007 | Levene et al. |
| 7,189,361 B2 | 3/2007 | Carson |
| 7,197,196 B2 | 3/2007 | Lin et al. |
| 7,199,357 B1 | 4/2007 | Oldham et al. |
| 7,209,836 B1 | 4/2007 | Schermer et al. |
| 7,227,128 B2 | 6/2007 | Sagatelyan |
| 7,248,771 B2 | 7/2007 | Schmidt et al. |
| RE39,772 E | 8/2007 | Herron et al. |
| 7,257,141 B2 | 8/2007 | Chua |
| 7,271,896 B2 | 9/2007 | Chan et al. |
| 7,302,146 B2 | 11/2007 | Turner et al. |
| 7,302,348 B2 | 11/2007 | Ghosh et al. |
| 7,315,019 B2 | 1/2008 | Turner et al. |
| 7,323,681 B1 | 1/2008 | Oldham et al. |
| 7,385,460 B1 | 6/2008 | Wang et al. |
| 7,400,380 B2 | 7/2008 | Hahn |
| 7,443,489 B2 | 10/2008 | Natan |
| 7,476,504 B2 | 1/2009 | Turner |
| 7,486,865 B2 | 2/2009 | Foque et al. |
| 7,499,094 B2 | 3/2009 | Kuriyama |
| 7,501,241 B2 | 3/2009 | Matsushita et al. |
| 7,537,734 B2 | 5/2009 | Reichert et al. |
| 7,539,366 B1 | 5/2009 | Baks et al. |
| 7,626,704 B2 | 12/2009 | Lundquist et al. |
| 7,630,063 B2 | 12/2009 | Padmanabhan et al. |
| 7,630,073 B2 | 12/2009 | Lundquist et al. |
| 7,709,808 B2 | 5/2010 | Reel et al. |
| 7,767,441 B2 | 8/2010 | Chiou et al. |
| 7,811,810 B2 | 10/2010 | Chiou et al. |
| 7,817,281 B2 | 10/2010 | Kiesel et al. |
| 7,820,983 B2 | 10/2010 | Lundquist et al. |
| 7,834,329 B2 | 11/2010 | Lundquist et al. |
| 7,838,847 B2 | 11/2010 | Lundquist et al. |
| 7,907,800 B2 | 3/2011 | Foquet et al. |
| 7,924,374 B2 | 4/2011 | Chang |
| 8,053,742 B2 | 11/2011 | Lundquist et al. |
| 8,207,509 B2 | 6/2012 | Lundquist et al. |
| 8,247,216 B2 | 8/2012 | Zaccarin et al. |
| 8,274,040 B2 | 9/2012 | Zhong et al. |
| 8,411,375 B2 | 4/2013 | Lenchenkov |
| 8,465,699 B2 | 6/2013 | Fehr et al. |
| 8,467,061 B2 | 6/2013 | McCaffrey et al. |
| 8,471,219 B2 | 6/2013 | Lundquist et al. |
| 8,564,095 B2 | 10/2013 | Huang et al. |
| 8,618,507 B1 | 12/2013 | Lundquist et al. |
| 8,747,751 B2 | 6/2014 | Duer et al. |
| 8,748,947 B2 | 6/2014 | Milgrew |
| 8,906,320 B1 | 12/2014 | Eltoukhy et al. |
| 8,994,946 B2 | 3/2015 | McCaffrey et al. |
| 9,029,802 B2 | 5/2015 | Lundquist et al. |
| 9,096,898 B2 | 8/2015 | Williams et al. |
| 9,223,084 B2 | 12/2015 | Grot et al. |
| 9,372,308 B1 | 6/2016 | Saxena et al. |
| 9,551,030 B2 | 1/2017 | Turner et al. |
| 2001/0041025 A1 | 11/2001 | Farahi |
| 2002/0034457 A1 | 3/2002 | Reichert et al. |
| 2002/0094147 A1 | 7/2002 | Herron et al. |
| 2002/0110839 A1 | 8/2002 | Bach et al. |

(56) References Cited

U.S. PATENT DOCUMENTS

| | | |
|---|---|---|
| 2002/0113213 A1 | 8/2002 | Amirkhanian et al. |
| 2002/0146047 A1 | 10/2002 | Bendett et al. |
| 2002/0155592 A1 | 10/2002 | Kelleher et al. |
| 2003/0044160 A1 | 3/2003 | Jones et al. |
| 2003/0044781 A1 | 3/2003 | Korlach et al. |
| 2003/0132406 A1 | 7/2003 | Waldhausl et al. |
| 2003/0133681 A1 | 7/2003 | Bozhevolnyi |
| 2003/0138180 A1 | 7/2003 | Kondo |
| 2003/0174324 A1 | 9/2003 | Sandstrom |
| 2003/0174992 A1 | 9/2003 | Levene et al. |
| 2003/0201462 A1 | 10/2003 | Pommer et al. |
| 2003/0210399 A1 | 11/2003 | Bahatt et al. |
| 2003/0214057 A1 | 11/2003 | Huang |
| 2004/0040868 A1 | 3/2004 | Denuzzio et al. |
| 2004/0046128 A1 | 3/2004 | Abel et al. |
| 2004/0197793 A1 | 10/2004 | Hassibi et al. |
| 2004/0234417 A1 | 11/2004 | Schienle et al. |
| 2004/0249227 A1 | 12/2004 | Klapproth et al. |
| 2004/0257374 A1* | 12/2004 | McGowan .......... G09G 5/393 345/547 |
| 2005/0006607 A1 | 1/2005 | Winter et al. |
| 2005/0014178 A1 | 1/2005 | Holm-Kennedy |
| 2005/0024510 A1 | 2/2005 | Lapstun et al. |
| 2005/0089993 A1 | 4/2005 | Boccazzi |
| 2005/0110989 A1 | 5/2005 | Schermer et al. |
| 2005/0135974 A1 | 6/2005 | Harvey et al. |
| 2005/0175273 A1 | 8/2005 | Iida et al. |
| 2005/0201899 A1 | 9/2005 | Weisbuch |
| 2005/0206895 A1 | 9/2005 | Salmelainen |
| 2006/0060766 A1 | 3/2006 | Turner et al. |
| 2006/0088818 A1 | 4/2006 | Beynon et al. |
| 2006/0098927 A1 | 5/2006 | Schmidt et al. |
| 2006/0103850 A1 | 5/2006 | Alphonse et al. |
| 2006/0183145 A1 | 8/2006 | Turner |
| 2006/0251371 A1 | 11/2006 | Schmidt et al. |
| 2006/0252070 A1 | 11/2006 | Boege et al. |
| 2006/0273245 A1 | 12/2006 | Kim et al. |
| 2007/0036511 A1 | 2/2007 | Lundquist et al. |
| 2007/0099212 A1 | 5/2007 | Harris |
| 2007/0134128 A1 | 6/2007 | Korlach |
| 2007/0146701 A1 | 6/2007 | Kiesel et al. |
| 2007/0188746 A1 | 8/2007 | Kraus et al. |
| 2007/0196815 A1 | 8/2007 | Lappe et al. |
| 2007/0279727 A1 | 12/2007 | Gandhi et al. |
| 2007/0281288 A1 | 12/2007 | Belkin et al. |
| 2008/0002929 A1 | 1/2008 | Bowers et al. |
| 2008/0013877 A1 | 1/2008 | Schmidt et al. |
| 2008/0020938 A1 | 1/2008 | Kaplan |
| 2008/0037008 A1 | 2/2008 | Shepard et al. |
| 2008/0039339 A1 | 2/2008 | Hassibi |
| 2008/0056950 A1 | 3/2008 | Weisbuch et al. |
| 2008/0062290 A1 | 3/2008 | Lahav et al. |
| 2008/0081769 A1 | 4/2008 | Hassibi |
| 2008/0117421 A1 | 5/2008 | Yamaguchi et al. |
| 2008/0152280 A1 | 6/2008 | Lundquist |
| 2008/0161195 A1 | 7/2008 | Turner et al. |
| 2008/0176769 A1 | 7/2008 | Rank et al. |
| 2008/0212960 A1 | 9/2008 | Lundquist |
| 2008/0220537 A1 | 9/2008 | Foquet |
| 2008/0240543 A1 | 10/2008 | Budach et al. |
| 2008/0241866 A1 | 10/2008 | Korlach et al. |
| 2008/0260577 A1 | 10/2008 | Shirai et al. |
| 2008/0308888 A1 | 12/2008 | Lee |
| 2009/0024331 A1* | 1/2009 | Tomaney .......... C12Q 1/6869 702/19 |
| 2009/0139576 A1 | 6/2009 | Crenshaw |
| 2009/0146076 A1 | 6/2009 | Chiou et al. |
| 2009/0152664 A1 | 6/2009 | Klem et al. |
| 2009/0181396 A1 | 7/2009 | Luong et al. |
| 2009/0195784 A1 | 8/2009 | Ogura et al. |
| 2009/0208957 A1 | 8/2009 | Korlach et al. |
| 2009/0247414 A1 | 10/2009 | Obradovic et al. |
| 2009/0253130 A1 | 10/2009 | Yoo et al. |
| 2009/0296188 A1 | 12/2009 | Jain et al. |
| 2009/0298075 A1 | 12/2009 | Travers et al. |
| 2009/0311774 A1 | 12/2009 | Chiou et al. |
| 2009/0321244 A1 | 12/2009 | Smith |
| 2009/0323014 A1 | 12/2009 | Cunningham et al. |
| 2010/0009872 A1 | 1/2010 | Eid et al. |
| 2010/0065726 A1* | 3/2010 | Zhong .................. G01N 21/648 250/227.24 |
| 2010/0099100 A1 | 4/2010 | Zaccarin et al. |
| 2010/0111475 A1 | 5/2010 | Lu et al. |
| 2010/0121582 A1 | 5/2010 | Pan et al. |
| 2010/0163521 A1 | 7/2010 | Balamane et al. |
| 2010/0173394 A1 | 7/2010 | Colston et al. |
| 2010/0243449 A1 | 9/2010 | Oliver |
| 2010/0255488 A1 | 10/2010 | Kong et al. |
| 2010/0256918 A1 | 10/2010 | Chen et al. |
| 2010/0295083 A1 | 11/2010 | Celler |
| 2011/0069389 A1 | 3/2011 | Shpunt |
| 2011/0079704 A1 | 4/2011 | Yu et al. |
| 2011/0117637 A1 | 5/2011 | Gray et al. |
| 2011/0165652 A1* | 7/2011 | Hardin .................. C07H 19/10 435/194 |
| 2011/0183320 A1 | 7/2011 | Flusberg et al. |
| 2011/0183409 A1 | 7/2011 | Newby et al. |
| 2011/0195406 A1* | 8/2011 | Sorenson ............ C12N 9/1252 435/6.1 |
| 2011/0201099 A1 | 8/2011 | Anderson et al. |
| 2011/0210094 A1 | 9/2011 | Gray et al. |
| 2011/0222179 A1 | 9/2011 | Monadgemi |
| 2011/0223590 A1 | 9/2011 | Chiou et al. |
| 2011/0257040 A1 | 10/2011 | Turner et al. |
| 2011/0306039 A1 | 12/2011 | Chioou et al. |
| 2011/0306143 A1 | 12/2011 | Chiou et al. |
| 2012/0014837 A1 | 1/2012 | Fehr et al. |
| 2012/0019828 A1 | 1/2012 | McCaffrey et al. |
| 2012/0021525 A1 | 1/2012 | Fehr et al. |
| 2012/0052506 A1 | 3/2012 | Yue et al. |
| 2012/0058469 A1 | 3/2012 | Shen et al. |
| 2012/0058473 A1 | 3/2012 | Yue et al. |
| 2012/0058482 A1 | 3/2012 | Shen et al. |
| 2012/0077189 A1 | 3/2012 | Shen et al. |
| 2012/0085894 A1 | 4/2012 | Zhong et al. |
| 2012/0156100 A1 | 6/2012 | Tsai et al. |
| 2012/0330566 A1* | 12/2012 | Chaisson ............... G16B 30/00 702/20 |
| 2013/0043552 A1 | 2/2013 | Lazarov et al. |
| 2013/0060482 A1 | 3/2013 | Sikora et al. |
| 2013/0148682 A1 | 6/2013 | Zhang et al. |
| 2013/0203046 A1 | 8/2013 | Wiltsie |
| 2013/0251592 A1* | 9/2013 | Mccaffrey .......... G01N 21/6428 422/82.05 |
| 2013/0338010 A1 | 12/2013 | Turner et al. |
| 2014/0193331 A1 | 7/2014 | Naczynski et al. |
| 2014/0241682 A1 | 8/2014 | Sandhu et al. |
| 2014/0287964 A1 | 9/2014 | Lundquist et al. |
| 2014/0303016 A1 | 10/2014 | Tomaney et al. |
| 2014/0322656 A1 | 10/2014 | Wright et al. |
| 2014/0353577 A1 | 12/2014 | Agarwaql et al. |
| 2015/0286060 A1 | 10/2015 | Roh et al. |
| 2016/0154165 A1 | 6/2016 | Grot et al. |
| 2016/0273034 A1 | 9/2016 | Lundquist et al. |

FOREIGN PATENT DOCUMENTS

| | | |
|---|---|---|
| EP | 1871902 B1 | 10/2006 |
| EP | 2362209 A2 | 8/2011 |
| FR | 2783919 A1 | 3/2000 |
| KR | 10-2005-0088782 A | 9/2005 |
| WO | WO 1991/006678 A1 | 5/1991 |
| WO | WO 2001/003833 A1 | 1/2001 |
| WO | WO 2001/016375 A2 | 3/2001 |
| WO | WO 2004/100068 A2 | 11/2004 |
| WO | WO 2006/116726 A2 | 2/2006 |
| WO | WO 2006/135782 A2 | 12/2006 |
| WO | WO 2007/002367 A2 | 1/2007 |
| WO | WO 2007/011549 A1 | 1/2007 |
| WO | WO 2008/002765 A2 | 1/2008 |
| WO | WO 2009/001988 A1 | 12/2008 |
| WO | WO 2009/056065 A1 | 5/2009 |
| WO | WO 2009/131535 A1 | 10/2009 |

(56) References Cited

FOREIGN PATENT DOCUMENTS

| | | |
|---|---|---|
| WO | WO 2009/149125 A2 | 12/2009 |
| WO | WO 2010/009543 A1 | 1/2010 |
| WO | WO 2010/051773 A1 | 5/2010 |
| WO | WO 2010/102567 A1 | 9/2010 |
| WO | WO 2010/115147 A2 | 10/2010 |
| WO | WO 2011/076132 A2 | 6/2011 |
| WO | WO 2014/031157 A1 | 2/2014 |
| WO | WO 2014/186604 A1 | 11/2014 |

OTHER PUBLICATIONS

Brodtkorb, A. R., Dyken, C., Hagen, T. R., Hjelmervik, J. M. & Storaasli, O. O. State-of-the-art in heterogeneous computing. Scientific Programming 18, 1-33 (2010).*

Da Silva, B. et al. Comparing and combining GPU and FPGA accelerators in an image processing context. in International Conference on Field Programmable Logic and Applications 6-9 (2013).*

Stevens, K., Chen, H., Filiba, T., McMahon, P. & Song, Y. S. SeqHive: A reconfigurable computer cluster for genome resequencing. International Conference on Field Programmable Logic and Applications 442-447 (2010).*

Xilinx, Inc. Bus Master DMA Performance Demonstration Reference Design for the Xilinx Endpoint PCI Express® Solutions. Technical Documentation. Dec. 3, 2009. Excerpt of pp. 1-2.*

Meng, P., Jacobsen, M. & Kastner, R. FPGA-GPU-CPU heterogenous architecture for real-time cardiac physiological optical mapping. in International Conference on Field-Programmable Technology 37-42 (IEEE, 2012).*

Lindholm, E.; Nickolls, J.; Oberman, S.; Montrym, J. Nvidia Tesla: A Unified Graphics and Computing Architecture. IEEE Micro 2008, 28 (2), 39-55.*

Rahman, R. Introduction to Xeon Phi Architecture. In Intel® Xeon Phi™ Coprocessor Architecture and Tools; Apress: Berkeley, CA, 2013; pp. 3-14.*

Timmons, M.; Feith, W. High-Performance Machine Vision Systems Using Xilinx 7 Series Technology. Whitepaper. XILINX, Inc. Jul. 13, 2014. 18 pages.*

Abbas et al., "Sensitivity Comparison of Surface Plasmon Resonance and Plasmon-Waveguide Resonance Biosensors", Sens. Actuators B Chem., v. 156, issue 1, p. 169-175 (2011).

Barrios, "Ultrasensitive Nanomechanical Photonic Sensor Based on Horizontal Slot-Waveguide Resonator", IEEE Photon Technol. Lett., v. 18, issue 22, p. 2419-2421 (2006).

Barrios et al., "Slot-Waveguide Biochemical Sensor", Optics Letters v. 32, issue 21, p. 3080-3082 (2007).

Barrios et al., "Label-Free Optical Biosensing with Slot-Waveguides", Optics Letters v. 33(7), p. 708 (2008).

Bernini et al., "Polymer-on-glass waveguide structure for efficient fluorescence-based optical biosensors" Proc. SPIE (2005) 5728:101-111.

Boiarski et al., "Integrated-optic sensor with macro-flow cell" Proc. SPIE (1992) 1793:199-211.

Budach et al., "Planar waveguides as high-performance sensing platforms for fluorescence-based multiplexed oligonucleotide hybridization assays" Anal. Chem. (1999) 71(16):3347-3355.

Chen et al., "Internal-Switching and Self-Optical Parametric Oscillation in a Two-Dimensional Periodically Poled Nd:MgO:LiNbO3 Laser", Optics Letters, v. 37(14), p. 2814-2816 (2012).

Cottier et al., "Thickness-modulated waveguides for integrated optical sensing" Proc. SPIE (2002) 4616:53-63.

Deopura, M. et al., "Dielectric omnidirectional visible reflector" Optics Lett (2001) 26(15):1197-1199.

Duveneck et al., "Planar waveguides for ultra-high sensitivity of the analysis of nucleic acids" Anal Chem Acta (2002) 469:49-61.

Eid, J., et al., "Real-Time DNA Sequencing from Single Polymerase Molecules," Science, vol. 323, p. 133-138 (Jan. 2, 2009).

Feldstein et al., "Array Biosensor: optical and fluidics systems" J. Biomed Microdev. (1999) 1:139-153.

Feng et al., "Optical Field Concentration in Low-Index Waveguides", IEEE J. Quantum Electron., V. 42(9), p. 885-890 (2006).

Feng et al., "Low-Loss Compact-Size Slotted Waveguide Polarization Rotator and Transformer", Optics Letters, v. 32(15), p. 2131-2133 (2007).

Fink, Y. et al., "A dielectric omnidirectional reflector" Science (1998) 282:1679-1682.

Fonollosa et al., "Fresnel Lenses: Study and Fabrication in Silicon Technology for Medium-IR Applications", Proc. SPIE 6186, MEMS, MOEMS, and Micromachining II, 61860R (Apr. 21, 2006); doi: 10.1117/12.662793; https://doi.org/10.1117/12.662793.

Golub, "Laser Beam Splitting by Diffractive Optics", Optics & Photonics News 36-41, (Feb. 2004).

Han, K.-H., et al., "An Active Microfluidic System Packaging Technology", Sensors and Actuators B 122, p. 337-346, 2007.

Herron et al., "Orientation and Activity of Immobilized Antibodies" Biopolymers at Interfaces 2nd Ed (2003) Surfactant Science Series vol. 110, Marcel Dekker, NY pp. 115-163.

Kumbhakar, M. "Single-Molecule Detection in Exploring Nanoenvironments: an Overview," J. of Photochemistry and Photobiology, n. 5, p. 113-137 (2004).

Laurell et al., "Laser-Written Waveguides in KTP for Broadband Type II Second Harmonic Generation", Optics Express, v. 20, n. 20, p. 22308 (2012).

Leger et al. "Coherent Laser Beam Addition: An Application of Binary-Optics Technology", The Lincoln Laboratory Journal 1(2), p. 225-246 (1988).

Levene, M.J. et al., "Zero-mode waveguides for single-molecule analysis at high concentrations" Science (2003) 299:682-686.

Mortazavi et al., "Quasi-Phase-Matched Frequency Doubling in Bulk Periodic Polymeric Structures" Optics Letters, v. 19, issue 17, p. 1290-1292 (1994).

Nava et al., "Integrated Frequency Shifter in Periodically Poled Lithium Tantalate Waveguide", Electronics Letters, v. 46, issue 25, p. 1686 (2010).

Ottesen et al., "Microfluidic Digital PCR Enables Multigene Analysis of Individual Environmental Bacteria," Science, 2006, v. 314, p. 1464.

Pan et al., "Tuning Visible Light Generation Based on Multi-Channel Quasi-Periodically Poled $LiTaO_3$", Optics Communications, v. 284, issue 1, p. 429 (2011).

Pang et al., "Fluorescence Microscopy Imaging with a Fresnel Zone Plate Array Based Optofluidic Microscope", Lab Chip, v. 11, Issue 21, p. 3698-3702 (2011).

Psaltis, Demetri, et al., "Developing Optofluidic Technology through the Fusion of Microfluidics and Optics," Nature, v. 442, p. 381-386, Jul. 27, 2006.

Robinson et al., "On-Chip Gas Detection in Silicon Optical Microcavities", Optics Express, v. 16, n. 6, p. 4296 (2008).

Sahin et al., J. Nanophoton. 5:051812 (2004).

Salama et al., "Modeling and simulations of luminescence detection platforms" Biosensors & Bioelectronics (2004) 19:1377-1386.

Satoh, et al., "On-Chip Microfluidic Transport and Bio/Chemical Sensing Based on Electrochemical Bubble Formation", Sensors and Actuators B 123, p. 1153-1160, 2007.

Song et al., "Polarization Properties of Surface Plasmon Enhanced Photoluminescence from a Single Ag Nanowire", Optics Express, v. 20, n. 20, p. 22290 (2012).

Sun et al., "Horizontal Single and Multiple Slot Waveguides: Optical Transmission at $\lambda = 1550$ nm" Optics Express, v. 15, n. 26, p. 17967 (2007).

Wang, et al., "Generation of Radially and Azimuthally Polarized Light by Optical Transmission Through Concentric Circular Nanoslits in AG Films," Optics Express, 2010, vol. 18, issue 1, 63-71.

Weissman et al., "Mach-Zehnder type, evanescent-wave bio-sensor, in ion-exchanged glass, using periodically segmented waveguide" Proc. Spie (1999) 3596:210-216.

Wu et al., "DNA and protein microarray printing on silicon nitride waveguide surfaces" Biosensors and Bioelectronics (2006) 21:1252-1263.

Yang, Z. et al., "A World-to-Chip Socket for Microfluidic Prototype Development" Electrophoresis, v. 23, p. 3474-3478, Jan. 1, 2002.

(56) References Cited

OTHER PUBLICATIONS

Yang, Z. et al., "Socket with Built-In Valves for the Interconnection of Microfluidic Chips to Macro Constituents", J. of Chromatography, v. 1013, No. 1-2, p. 29-33, Sep. 26, 2003.
Yao et al., "Nonlinear Optics and Solid-State Lasers", Springer-Verlag Berlin Heidelberg, Chapter 5 (2012).
Aluru, Srinivas, et al., A Review of Hardware Acceleration for Computational Genomics, IEEE Design & Test, IEEE, Piscataway, NJ, USA, vol. 31, No. 1, (Dec. 5, 2013), pp. 19-30.

* cited by examiner

PRIMARY ANALYSIS PIPELINE 500'

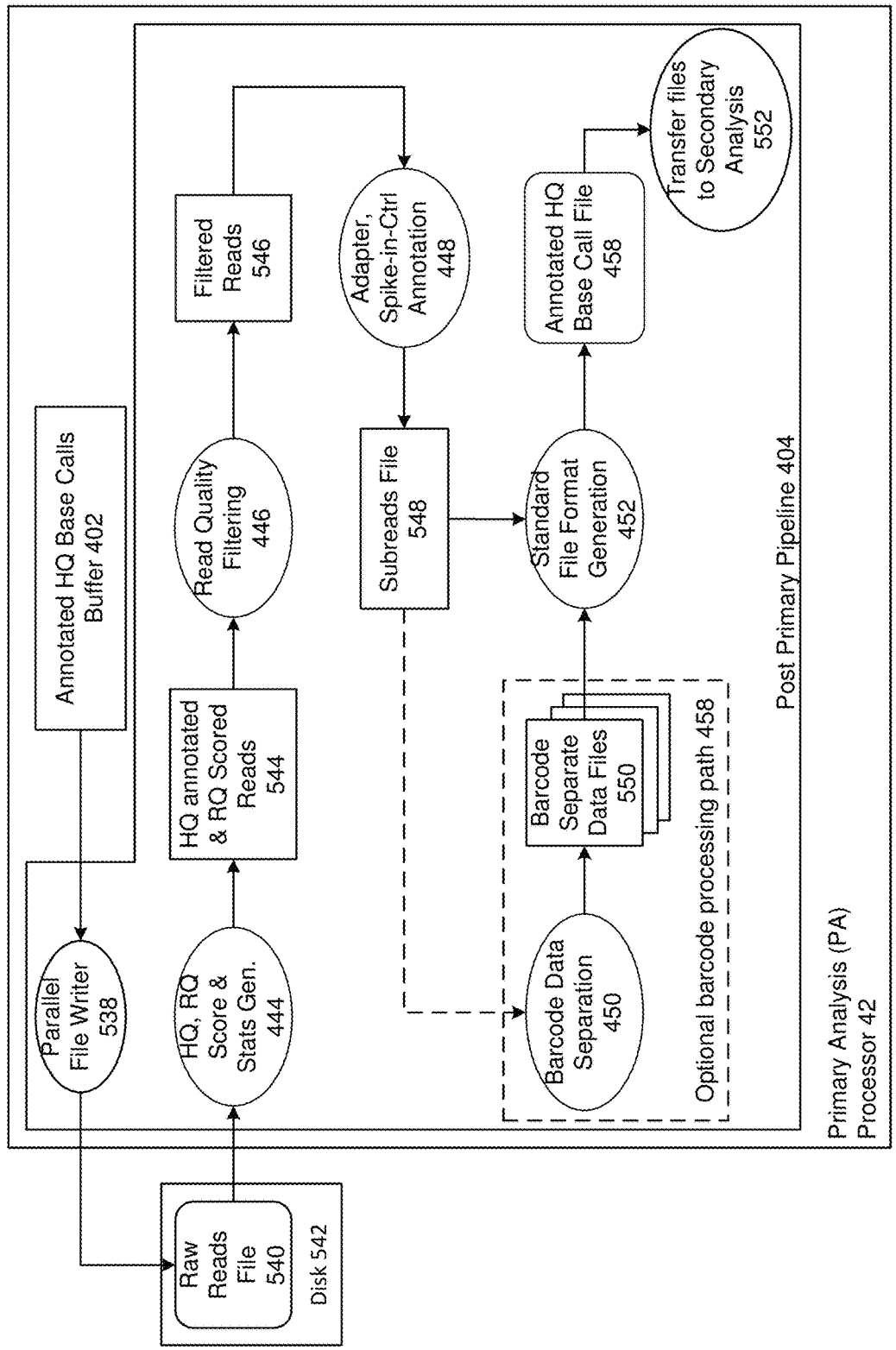

MULTIPROCESSOR PIPELINE ARCHITECTURE

CROSS-REFERENCE TO RELATED APPLICATIONS

This application claims the benefit of priority to Provisional Patent Application Ser. No. 62/158,078 (01018100), filed May 7, 2015, entitled "Multiprocessor Pipeline Architecture"; and Provisional Patent Application Ser. No. 62/260,995 (01018101), filed Nov. 30, 2015, entitled "Multiprocessor Pipeline Architecture", is related to U.S. Pat. Nos. 8,467,061 and 8,649,011, both entitled "Integrated Analytical System and Method"; and to U.S. Provisional Patent Application Ser. No. 62/042,793 (01018000), filed Aug. 27, 2014, entitled "Arrays of Integrated Analytical Devices and Methods for Production"; each assigned to the assignee of the present application, and incorporated herein will by reference.

BACKGROUND OF THE INVENTION

Advances in biomolecule sequence determination, in particular with respect to nucleic acid and protein samples, has revolutionized the fields of cellular and molecular biology. A sequencing instrument, such as a DNA sequencer, is used to automate biomolecule sequence determination, e.g., a nucleic acid sequencing. Given a sample of DNA, a DNA sequencer is used to determine the composition of the biomolecule, such as the base composition of a nucleic acid molecule with respect to the order of the four bases: adenine, guanine, cytosine, and thymine. The order of the DNA bases is reported as a text string, called a read. Some DNA sequencers can be also considered optical instruments as they analyze light signals originating from fluorochromes attached to nucleotides. Third-generation DNA sequencers such as SMRT and Oxford Nanopore measure the addition of nucleotides to a single DNA molecule in real time. Because of limitations in DNA sequencer technology these reads are short compared to the length of a genome therefore the reads must be assembled into longer contigs.

Typically, the final assembly of a genome is accomplished on other computational resources off the sequencing instrument. Final assembly is required on other computational resources due to multiple reasons including the following: 1) a need to combine the results from multiple instrument runs or acquisitions (sometimes from other physical instruments), 2) the computational and memory resources required to accomplish the assembly are not available on the sequencing instrument, whether the sequencer instrument performs denovo shotgun assembly or an assembly aided by a reference sequence, 3) the use of third party assembler packages designed for running on cluster configurations, 4) assembly algorithms which are not designed to process data as it streams off the sequencing instrument, 5) assembly algorithms are designed to run on conventional computer architectures that are incapable of providing the computational resources necessary to perform assembly in real time.

What is desired is a sequencing system having a computational architecture that supports complete genome assembly from raw streaming data produced by a sequencing instrument in real time, where the final result is the finished genome sequence. It is also desirable that the architecture is flexible and easily scalable to increase the throughput of the system, while at the same time reducing the costs associated with the manufacturing and usage of the system.

BRIEF SUMMARY OF THE INVENTION

The exemplary embodiments are generally directed to multiprocessor pipeline architectures and methods that convert signals from sequencing sample acquisition into sequence data, comprising: a custom coprocessor card configured to directly receive a stream of serialized sensor data generated by an image sensor, wherein the sensor data represents frame-by-frame intensity values for pixels comprising the image sensor, wherein the image sensor captures images of light emitted from a plurality of reaction cells of a removable integrated sequencing chip; a first coprocessor that continually receives the stream of serialized sensor data and transposes the frame-by-frame intensity values into reaction cell chunks, each of the reaction cell chunks representing movie data of the pixel intensity values of a corresponding reaction cell across the frames over a predetermined time window; a buffer that repeatedly receives the reaction cell chunks and stores in contiguous memory locations the reaction cell chunks for each respective reaction cell over a larger predetermined time window to create larger reaction cell chunks; and a plurality of second coprocessors that retrieve the larger reaction cell chunks from the buffer and convert, in parallel, the pixel intensity values into base-by-base sequence data even as additional reaction cell chunks are received by the buffer, such that the second coprocessors begin raw base calling before all the sensor data for the sequencing sample acquisition is obtained.

In yet another aspect, a multiprocessor pipeline architecture, comprises: 1) a sequencing instrument, comprising: a reservoir containing a solution comprising a sequencing reaction mixture including a sample to be sequenced and reagents for carrying out the nucleic acid sequencing reaction; an illumination source that provides illumination; a removable integrated sequencing chip in contact with the reservoir, the integrated sequencing chip comprising a plurality of analytical devices, each analytical device comprising a reaction cell, a waveguide, optical elements, and an image sensor, wherein the waveguide channels the illumination to the reaction cell, resulting in emission of light from the reaction cells that is passed by the optical elements to the image sensor that detects the light and converts the light into sensor data represented as frame-by-frame intensity values for each of the pixels comprising the image sensor, the sequencing chip having a coprocessor that serializes and outputs the stream of sensor data; and 2) a primary analysis server coupled to the sequencing instrument that converts the stream of sensor data into base calls, the primary analysis server comprising: a custom coprocessor daughter card configured to directly receive the stream of serialized sensor data over a serial cable; at least one coprocessor that transposes the frame-by-frame intensity values into reaction cell chunks, each representing movie data of the pixel intensity values of a corresponding reaction cell across the frames over a predetermined time window; a buffer that repeatedly receives reaction cell chunks and stores in contiguous memory locations the reaction cell chunks for each respective reaction cell over a larger predetermined time window to create larger reaction cell chunks; and wherein the at least one coprocessor retrieves the larger reaction cell chunks from the buffer and converts the pixel intensity values into base-by-base sequence data such that the conversion begins before all the sensor data for the sequencing sample acquisition is obtained.

The invention and various specific aspects and embodiments will be better understood with reference to the following detailed descriptions and figures, in which the invention is described in terms of various specific aspects and embodiments. These are provided for purposes of clarity and should not be taken to limit the invention. The invention and aspects thereof may have applications to a variety of types of methods, devices, and systems not specifically disclosed herein.

BRIEF DESCRIPTION OF SEVERAL VIEWS OF THE DRAWINGS

FIGS. 5A, 5B and 5C are block diagrams illustrating in further detail the processing performed by the primary analysis pipeline.

DETAILED DESCRIPTION OF THE INVENTION

Various embodiments and components of the present invention employ signal and data analysis techniques that are familiar in a number of technical fields. For clarity of description, details of known analysis techniques are not provided herein. These techniques are discussed in a number of available reference works, such as: R. B. Ash. Real Analysis and Probability. Academic Press, New York, 1972; D. T. Bertsekas and J. N. Tsitsiklis. Introduction to Probability. 2002; K. L. Chung. Markov Chains with Stationary Transition Probabilities, 1967; W. B. Davenport and W. L Root. An Introduction to the Theory of Random Signals and Noise. McGraw-Hill, New York, 1958; S. M. Kay, Fundamentals of Statistical Processing, Vols. 1-2, (Hardcover—1998); Monsoon H. Hayes, Statistical Digital Signal Processing and Modeling, 1996; Introduction to Statistical Signal Processing by R. M. Gray and L. D. Davisson; Modern Spectral Estimation: Theory and Application/Book and Disk (Prentice-Hall Signal Processing Series) by Steven M. Kay (Hardcover—January 1988); Modern Spectral Estimation: Theory and Application by Steven M. Kay (Paperback—March 1999); Spectral Analysis and Filter Theory in Applied Geophysics by Burkhard Buttkus (Hardcover—May 11, 2000); Spectral Analysis for Physical Applications by Donald B. Percival and Andrew T. Walden (Paperback—Jun. 25, 1993); Astronomical Image and Data Analysis (Astronomy and Astrophysics Library) by J. L. Starck and F. Murtagh (Hardcover —Sep. 25, 2006); Spectral Techniques In Proteomics by Daniel S. Sem (Hardcover—Mar. 30, 2007); Exploration and Analysis of DNA Microarray and Protein Array Data (Wiley Series in Probability and Statistics) by Dhammika Amaratunga and Javier Cabrera (Hardcover—Oct. 21, 2003).

The exemplary embodiments provide a multiprocessor pipeline architecture capable of performing a complete genome assembly from raw streaming sensor data produced by sequencing instrument in real time with the final result of the instrument being the finished genome sequence, including per base quality values. The multiprocessor pipeline architecture is flexible and easily scalable to increase the throughput of the system, while at the same time reducing the costs associated with the manufacturing and usage of the system.

Figures 1A, 1B:
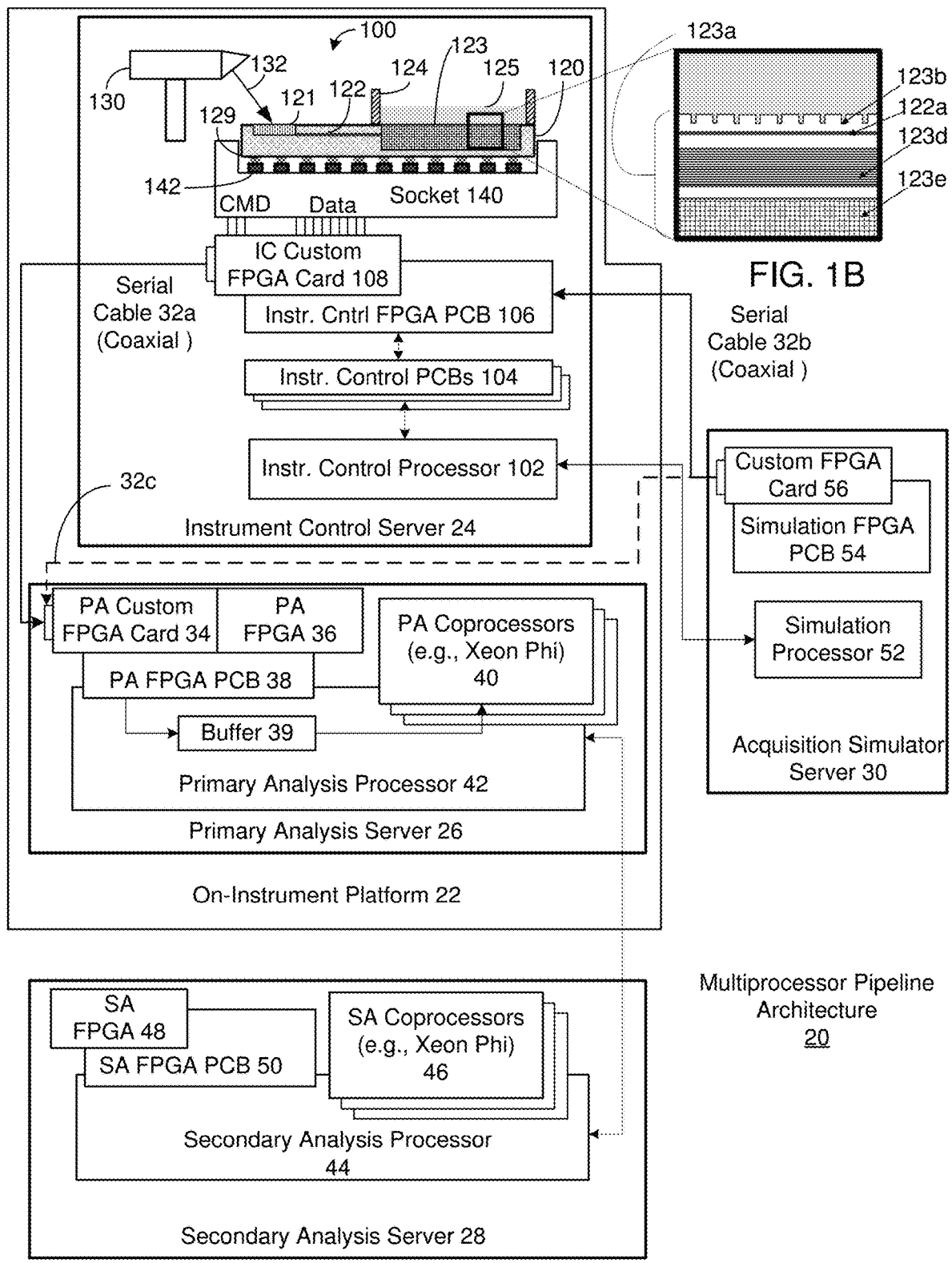
FIGS. 1A-1B are block diagrams showing hardware components the multiprocessor pipeline architecture in accordance with exemplary embodiments.

FIGS. 1A-1B are block diagrams showing hardware components the multiprocessor pipeline architecture in accordance with exemplary embodiments. In one embodiment, the multiprocessor pipeline architecture 20 includes an instrument control server 24, which in turn includes a single molecule (e.g., nucleic acid) sequencing instrument 100. The instrument control (IC) system 24 may also include an IC processor or CPU 102 coupled to one or more IC printed circuit boards (PCBs) 104.

Other components of the instrument control (IC) system 24 include an IC coprocessor PCB 106 coupled to the IC PCBs 104, and an IC custom coprocessor card 108 coupled to the IC coprocessor PCB 106. As is known in the art, the term coprocessor refers to a computer processor used to supplement the functions of a primary processor (e.g., a CPU). As used herein, "coprocessor" may refer to a field programmable gate array (FPGA), an application-specific integrated circuit (ASIC), a graphics processing unit (GPU), or any combination thereof. FIG. 1A shows an embodiment where certain coprocessors are labeled as FPGAs for clarity, but the exemplary embodiments are not to be limited to this particular embodiment.

Sequencing Instrument

The sequencing instrument 100 comprises a removable integrated sequencing chip 120 mounted in a socket 140. The sequencing chip 120 is generally directed to optical analyses of biological and/or chemical samples and reactions to provide for the simultaneous observation of multiple sequencing reactions in real time. In general, these optical analyses seek to gather and detect one or more optical signals, the appearance or disappearance of which, or localization of which, is indicative of a given chemical or biological reaction and/or the presence or absence of a given substance within a sample material. In some cases, the reactants, their products, or substance of interest (all of which are referred to as reactants herein) inherently present an optically detectable signal which can be detected. In other cases, reactants are provided with exogenous labeling groups to facilitate their detection. Useful labeling groups include fluorescent labels, luminescent labels, mass labels, light scattering labels, electrochemical labels (e.g., carrying large charge groups), metal labels, and the like.

The sequencing instrument 100 may further include a reservoir 124 and an illumination source 130, while the sequencing chip 120 may include one or more couplers 121, routing waveguides 122, and an analysis region 123. The reservoir 124 is in contact with the analysis region 123 and delivers to a solution 125 comprising a sequencing reaction mixture including a sample to be sequenced and reagents for carrying out the nucleic acid sequencing reaction. The reservoir 124 may be produced as part of the packaging for the analysis region 123

The illumination source 130 provides illumination in the form of one or more excitation light beams 132 to the sequencing chip 120. The illumination source 130 may comprise, for example, a laser or group of lasers. The one or more light beams 132 from the illumination source 130 are directed to one or more couplers 121 on the sequencing chip 120. The couplers 121 couple the light beams 132 to the routing waveguides 122, which propagate the light beams 132 to the analysis region 123 of the sequencing chip 120.

FIG. 1B illustrates a not-to-scale close-up example of the analysis region 123 of the sequencing chip 120. The analysis region 123 has an array of integrated analytical devices 123*a* for performing optical analysis, e.g., nucleic acid sequencing processes, that rely in part on non-spectral discrimination of differing signals, and optionally, in part on spectral distinction. The array of analytical devices 123*a* is useful, for example, in the large-scale sequencing of nucleic acids, including in particular, genomic sequencing. The nucleic acid sequencing can be single-molecule real-time nucleic acid sequencing.

The analysis region 123 may include anywhere from 1,000 to 100 million or more analytical devices 123*a*. In one embodiment, however, the analysis region 123 may include for example between 100,000 and 10 million, but preferably at least 500,000 analytical devices 123*a*. Such arrays can be produced by a variety of methods (See for example patent application Ser. No. 01/018,000 entitled "Arrays of Integrated Analytical Devices and Methods for Production," incorporated herein by reference).

While the components of each device and the configuration of the analytical devices 123*a* in the system may vary, each integrated analytical device 123*a* typically comprises, at least in part, the general structure described below. Each analytical device 123*a* typically includes a reaction cell 123*b*. "Reaction cell" generally refers to the location where the reactants are disposed, the location where the reaction of interest is occurring and from which the optical signals emanate. In some cases, the reaction cell 123*b* will have a biomolecule such as a polymerase enzyme immobilized within it, and a fluidic conduit from the reservoir 124 provides reagents across the reaction cells 123*b*. Thus, the reaction cell 123*b* may hold an analyte (i.e., the polymerase-template complex and associated fluorescent reactants) from which the optical signals emanate. In one embodiment, the reaction cell 123*b* comprises a nanowell or nanopore disposed in the surface layer. Such nanowells may constitute depressions in a substrate surface or apertures disposed through additional substrate layers to an underlying transparent substrate, e.g., as used in zero mode waveguide (ZMW) arrays (see, e.g., U.S. Pat. Nos. 7,181,122 and 7,907,800). In various respects, "analytical device" refers to the reaction cell 123*b* and associated components that are functionally connected.

Below the reaction cell 123*b* is a routing waveguide 122*a* that channels excitation illumination to the reaction cell 123*b* from below, illuminating reactants within the reaction cell 123*b*. Use of optical waveguides to illuminate reaction cells is described in e.g., U.S. Pat. No. 7,820,983 and U.S. Patent Application Publication No. 2012/0085894, which are each herein incorporated by reference. While a waveguide is shown here, other optical elements such as those provided elsewhere herein can be used to provide light from under the reaction cell.

In some embodiments, excitation illumination results in the emission of light from the reaction cell 123*b* in order to allow for optical measurements of sequencing. For example, an analyte (e.g., a polymerase-template complex with associated fluorescent reactants) disposed within a reaction cell 123*b* emits fluorescent light. For fluorescent analytes, at least a portion of the analyte sample is illuminated by an excitation light source, whereas other analytes, such as chemilunimescent or other such analytes, may not require an excitation light source.

The optical elements 123*d* are optically coupled to a detector, such as image sensor 123*e*, and pass the light emitted from within the reaction cell 123*b* to the image sensor 123*e*. The optical elements 123*d* may include any combination of apertures, lenses, prisms, mirrors filters, beam shaping elements, refractive material, rejection layers, and the like, depending upon the application. The light emitted from the reaction cell 123*b* may be further manipulated by the optical elements 123*d*, such as by diffractive beam shaping elements and color filtration layers, prior to reaching the image sensor 123*e*.

The emitted light passing through the optical elements 123*d* is detected by the image sensor 123*e* and converted into sensor data, comprising for example, pixel intensity values corresponding to optical signal pulses. Examples of the image sensor 123*e* may include CCD (charge-coupled device) and CMOS (complementary metal-oxide semiconductor) image sensors, both of which comprise an array of pixels/photodiodes that transform light into an electrical charge, the intensity of which is related to a color in the color spectrum. In one embodiment, the image sensor 123*e* may comprise at least 2 megapixels.

The ability to distinguish different signal components may be achieved through the use of, e.g., different filtered optical elements, or the inclusion of dispersive optical elements to differentially direct different spectral components of a signal to different pixels or different regions of the image sensor. The light from a particular reaction cell 123*b* is directed to the image sensor 123*e* such that a set of n pixels of the image sensor 123*e* is assigned to detect the amplitude or intensity values for one reaction cell 123*b*. For example, each reaction cell 123*b* could have one, two, three, four, or more pixels assigned to detect the intensity values emitted by the corresponding reaction cell 123*b*.

Figure 1C:
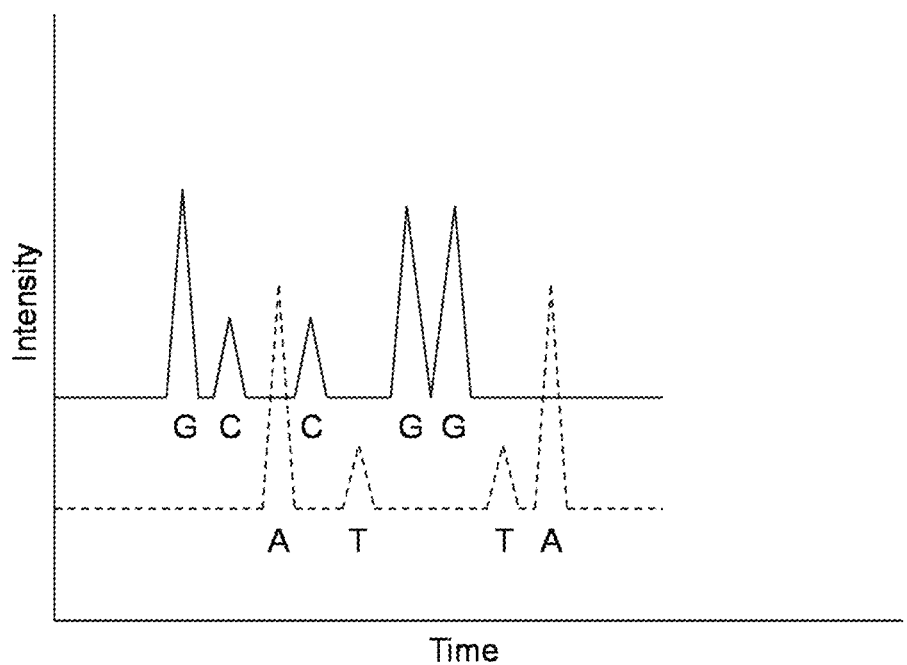
FIG. 1C is a diagram showing a signal output for a real time sequencing operation using a two color/two amplitude signal set from set of two pixels assigned to the reaction cell.

FIG. 1C is a diagram showing an exemplar signal output for a real time sequencing operation using a two color/two amplitude signal set from set of two pixels assigned to the reaction cell 123*b* over time (i.e., a time-series), where one trace (dashed) denotes signals associated with incorporation of A (high intensity signal) and T (lower intensity signal) bases, while the other signal trace (solid line), denotes the signals of a different emission spectrum, associated with G (high) and C (low) bases. The timing of incorporation and the identity of the base incorporated, as derived from the color channel and intensity of the signal, are then used to interpret the base sequence.

The exemplary system of FIG. 1A is configured for genomic sequencing. In operation generally, a sample from the reservoir 124 is delivered to analytical devices 123*a* for data collection. The instrument control processor 102, which is in communication with the sequencing chip 100, sets up data acquisition and instructs the image sensor 123*e* when to start capturing images. In response, the image sensor 123*e* may generate and output analog sensor data representing raw pixel data. In one embodiment, the analog sensor data may be a serialized 16 or 32 bit interface, with 11 bits per pixel. In one embodiment, the sensor data may be output at 100 frames per second, and include approximately 2 million pixels per frame. Thus, sensor data as a whole may represent frame-by-frame intensity values for the pixels comprising an image sensor 123*e*.

The sequencing chip 100 outputs the stream of sensor data from the image sensor 123e through contacts 129 on the sequencing chip 100, which may mate with contacts 142 on the socket 140. In one embodiment, the contacts 129 may comprise ball contacts, however other types of contacts may be used. In one embodiment, the socket 140 sends unmodified sensor data. In an alternative embodiment, the socket 140 may have electronics, such as a coprocessor (not shown), for altering the electrical trace signals before transmission to the primary analysis server 26.

In one embodiment, the analysis region 123 may be configured for single use as a consumable, and as such, discarded after sample acquisition and replaced with a new analysis region 123. Some sequencing experiments may require the use of multiple analysis region 123.

Although the sequencing chip 100 represents a technological advancement, conventional computational architectures are incapable of executing primary analysis and consensus base calling in real-time using the output of the sequencing chip 100. For example, the sensor data must be input into the computational architecture at a throughput too fast for conventional processors to even store the data to disk. In addition, to sequence the 3 billion base human genome where 30× coverage is needed to guarantee sufficient quality of the result, approximately 12 analysis regions 123 and corresponding acquisition processes may be required depending on the number of reaction cells 123b present in the analysis region 123. The amount of data produced during these multiple acquisition processes would require an amount of memory for storage and processing that would exceed the capacity of typical processor boards.

Multiprocessor Pipeline Architecture

The exemplary embodiments overcome the throughput and memory issues of conventional computational architectures presented by the sequencing chip 100 by providing a multiprocessor pipeline architecture that performs primary analysis through consensus base calling in substantially real-time. The multiprocessor pipeline architecture is designed to provide necessary parallelized computational resources and memory bandwidth needed to perform the entire genome assembly in "chunked" real time, as explained below. The overall system architecture has a modular design such that system can be scaled efficiently by adding or subtracting components, and therefore scales in cost depending on the size of the genome being sequenced.

Referring again to FIGS. 1A and 1B, details regarding the hardware aspects of the multiprocessor pipeline architecture will be described. According to the exemplary embodiment, the pipeline architecture has several subsystems, including the instrument control server 24, a primary analysis server 26, a secondary analysis server 28, and an optional acquisition simulator server 30. In one embodiment, the instrument control server 24 and the primary analysis server 26 may be housed in close proximity within an on-instrument platform 22. The acquisition simulator server 30 may communicate with the instrument control server 24, and the primary analysis server 26 may communicate with both the instrument control server 24 and the secondary analysis server 28.

The IC custom coprocessor card 108 in the instrument control system 102 receives the analog stream of raw pixel data output from the socket 140 of the sequencing instrument 100 and converts the analog stream of raw pixel data into a serialized bitstream of sensor data. In one embodiment, the sensor data is digitized and the data encoding may be modified to 8 bit or 10 bit to minimize errors. The format of the bitstream includes headers and data packets that form a complete image frame that will be reconstructed. Thus, the sensor data output by the IC custom coprocessor card 108 represents frame-by-frame intensities for each of the pixels of the image sensor 123e. The serialized bitstream of sensor data is output to the primary analysis server 26 for analysis and further processing.

The primary analysis server 26 carries out analysis to convert raw pixel data to base calls, after which, this data may be transferred off the on-instrument platform 22 and to the secondary analysis server 28 for secondary analysis, such as assembly. In another embodiment, if the primary analysis server 26 is provided with sufficient computational resources, then secondary analysis processing could also be performed within the primary analysis server 26.

In one embodiment, primary analysis server 26 comprises a primary analysis (PA) processor 42, a plurality of PA coprocessors 40, and a PA custom coprocessor card 34 and PA coprocessor 36 coupled to a PA coprocessor PCB 38. In one embodiment, the primary analysis server 26 may be on-instrument, as shown. In a second embodiment, the primary analysis server 26 may be located on-chip as part of the socket 140. And in a third embodiment the primary analysis server 26 may be located on a remote computer.

The secondary analysis server 44 carries out analysis to produce consensus base calling and assembly data. The architecture of the secondary analysis server 28 may be similar to that of the primary analysis server 26. In one embodiment, the secondary analysis server 26 comprises a secondary analysis (SA) processor 44, a plurality of SA coprocessors 46, and a SA coprocessor 40 coupled to a SA coprocessor PCB 50.

The acquisition simulator server 30 may be used to interface with the instrument control server 24. The acquisition simulation server 30 may comprise a simulation processor 52, and a simulation custom coprocessor card 56 coupled to a simulation coprocessor PCB 54. In one embodiment the acquisition simulator server 30 may transmit simulated sensor data to the instrument control server 24 to enable the instrument control server 24 to input simulated signal data/frames to the primary analysis server 26 via serial cable 32b without the need for the sequencing instrument 100. In a further embodiment, the acquisition simulator server 30 can also be connected directly to the PA custom FPGA card 34 in the primary analysis server 26 to input simulated signal data/frames via serial cable 32c without the need of the instrument control server 24.

In one exemplary embodiment, the PA coprocessor 36 and SA coprocessor 48 may comprise an FPGA or an ASIC, while the PA coprocessors 40 and SA coprocessors 46 may comprise an Intel Many Integrated Core Architecture coprocessor (i.e., Xeon Phi™) or the like. In an alternative embodiment, a combination FPGA and Xeon Phi coprocessors (or the like) could be used. In one exemplary embodiment, the use of FPGAs is preferred because FPGAs may aid in reducing the size and cost of the system during development. Once the system is configured in FPGA logic, ASICs may be created in place of the FPGAs. As an alternative to the Xeon Phi cards, GPU technology could be used. However, Xeon Phi cards present an advantage in terms of development environment.

Additionally, the PA processor 42, the SA processor 44, and the simulation processor 52 are coupled to respective memory, input/output (I/O), and network interface cards via a system bus or buses (not shown).

Figure 2:
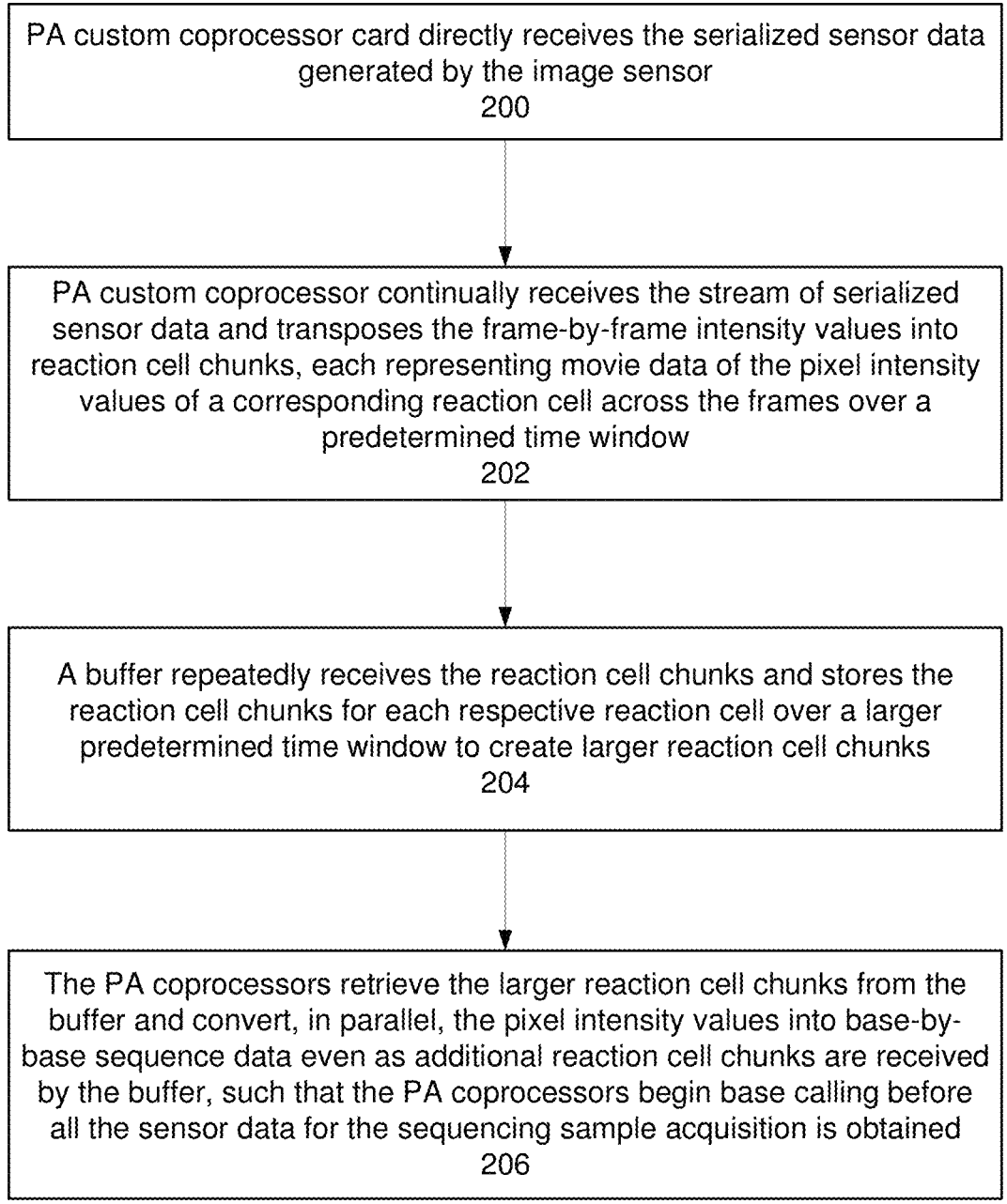
FIG. 2 is a flow diagram illustrating multiprocessor pipeline processing that converts sensor data from nucleic acid sequencing into sequence data according to an exemplary embodiment.

FIG. 2 is a flow diagram illustrating multiprocessor pipeline processing that converts sensor data from sequencing sample acquisition into sequence data according to an exemplary embodiment. The process may begin by the PA custom coprocessor card 34 directly receiving the serialized sensor data generated by the image sensor (block 200).

According to one aspect of the exemplary embodiment, the PA custom coprocessor card 34 and the IC custom coprocessor card 108 are customized by configuring the cards 34, 108 with cable connectors that mate with the serial cable 32a, which transfers the sensor data. Likewise, the custom coprocessor card 56 in the acquisition simulator server 30 is customized by configuring the card 56 with a cable connector that mates with respective serial cables 32a, 32b and 32c.

In one embodiment, the serial cables 32a, 32b and 32c comprise high speed cables, such a coaxial cable, a twisted pair copper wire, an optical fiber, and the like. In an alternative embodiment where the subsystems are separated over large distances, the serial cables 32a, 32b and 32c may optionally comprise Ethernet cables. If needed, the custom FPGA cards 128, 56, and 34 could be configured with more than one connection and accompanied logic if needed.

In one embodiment, the PA custom coprocessor card 34 and the PA coprocessor 36 are connected to the PA coprocessor PCB 38 via respective bus connectors. The PA custom coprocessor card 34 has wire connectors extending to the bus connector of the PA coprocessor PCB 38. In operation, the PA custom coprocessor card 34 receives the serialized bitstream of sensor data over the serial cable 32a from the IC custom coprocessor card 108 and converts the data into a format that can be input directly into the I/O ports of the PA coprocessor 36 via the connectors to the PA coprocessor PCB 38 that route the serial data to the correct pins of the PA coprocessor 36. In one embodiment the PA coprocessor PCB 38 may comprises a PCIe card and includes an edge connector designed to plug-in into a PCIe bus of the PA coprocessor PCB 38 motherboard (not shown). In an alternative embodiment, the primary analysis server 26 may be provided with a plurality of PA custom FPGA cards 34 if needed to satisfy a higher multiplex of reaction cells/ZMWs 123b data being output from the instrument control server 24. In other words, there could be multiple serial cables 32a connecting the instrument control server 24 to multiple PA custom FPGA cards 34 (or multiple cables input into a single PA custom FPGA card 34) depending on the serial transmission bandwidth limits and the processing limits of the FPGAs themselves.

The IC custom coprocessor card 108 the PA custom coprocessor card 34, and the custom coprocessor card 56 may include the same type of transceiver receiver chipset for digital communication. In the case of the PA custom coprocessor card 34, the transceiver chipset routes the data to traces on the PA coprocessor PCB 38, which then sends to data to the correct connector location hooked up to the PA coprocessor 36. In the embodiment where the serial cable 32a is a coaxial cable, the protocol governing the transmission of the data of the serial cable 32a may comprise an Aurora protocol, which is a Xilinx designed transmission protocol. For example, the PA custom coprocessor card 34 may use Aurora IP logic to transfer the digital data over the coaxial cable. However, other transmission protocols may also be used.

Through the use of the chipset, both the IC custom coprocessor card 108 and the PA custom coprocessor card 34 are capable of both sending and receiving digital data. According to another aspect of the exemplary embodiment, this enables the acquisition simulator server 30 to input simulation data/frames from the custom coprocessor card 56 and a serial cable 32b to the instrument control coprocessor PCB 106. The simulation data/frames are then passed through to the IC custom coprocessor card 108 and on to the PA custom coprocessor card 34. Running simulation data/frames to the multiprocessor pipeline allows operators to verify that the instrument control server 24 and primary analysis server 26 are operating properly.

Unlike conventional PCIe FPGA cards, the sensor data is being input directly into the PA custom coprocessor card 34 and the PA coprocessor 36 without first being input into the PA processor 42 or other computer and then passing the data to an FPGA. This is in contrast to conventional coprocessor cards in which image data is first input to a CPU and then passed to the FPGA, and requires the use of a frame grabber. The disadvantage of first going through a CPU is that it requires the use of a frame grabber board to take image data, which saps the processing power of the CPU just to input the data into the CPU and increases the cost of the system due to the cost involved with the need for additional CPU power to perform data processing on the same CPU.

In one exemplary embodiment, the PA custom coprocessor card 34 may comprise a customized version of a commercially available Conway FPGA Wolverine card. The PA coprocessor 36 and the SA coprocessor 48 may, for example, comprise a commercially available Xilinx Vertex FPGA, while the PA coprocessors 40 and the SA coprocessors 46 may comprise Intel Xeon Phi cards.

As stated above, the sensor data represents frame-by-frame intensity values for pixels comprising the image sensor, where a set of n pixels of the image sensor 123e is assigned to detect the intensity values emitted by each of the reaction cells 123b.

Referring again to FIG. 2, the PA custom coprocessor 36 continually receives the stream of serialized sensor data and transposes the frame-by-frame intensity values into reaction cell chunks, each representing movie data of the pixel intensity values of a corresponding reaction cell across the frames over a predetermined time window (Block 202).

In one embodiment, the reaction cell chunks (also referred to as chunked data sets) each represent movie data of the intensity values of the set of pixels assigned to a corresponding reaction cell across the frames. In an exemplary embodiment, the intensity values of the pixels for each of the reaction cell chunks are stored in contiguous memory locations.

The buffer 39 repeatedly receives reaction cell chunks and stores in contiguous memory locations the reaction cell chunks for each respective reaction cell over a larger predetermined time window to create larger reaction cell chunks, referred to herein as super reaction cell chunks (block 204).

The PA coprocessors 40 retrieve the larger reaction cell chunks from the buffer and convert, in parallel, the pixel intensity values into base-by-base sequence data even as additional reaction cell chunks are received by the buffer, such that the PA coprocessors 40 begin raw base calling before all the sensor data for the sequencing sample acquisition is obtained (block 206).

According to the exemplary embodiment, the PA coprocessor 36 (e.g., FPGA) transposes the frame-by-frame intensity values into the reaction cell chunks, while the PA coprocessors will (e.g., Xeon Phi chips) perform the base calling. However, as hardware designs continually improve, both processes may be performed by a single coprocessor (e.g., an FPGA/ASIC) or by multiple ones of the same type of coprocessors (e.g., all FPGA/ASICs or all Xeon Phi chips).

Figure 3:
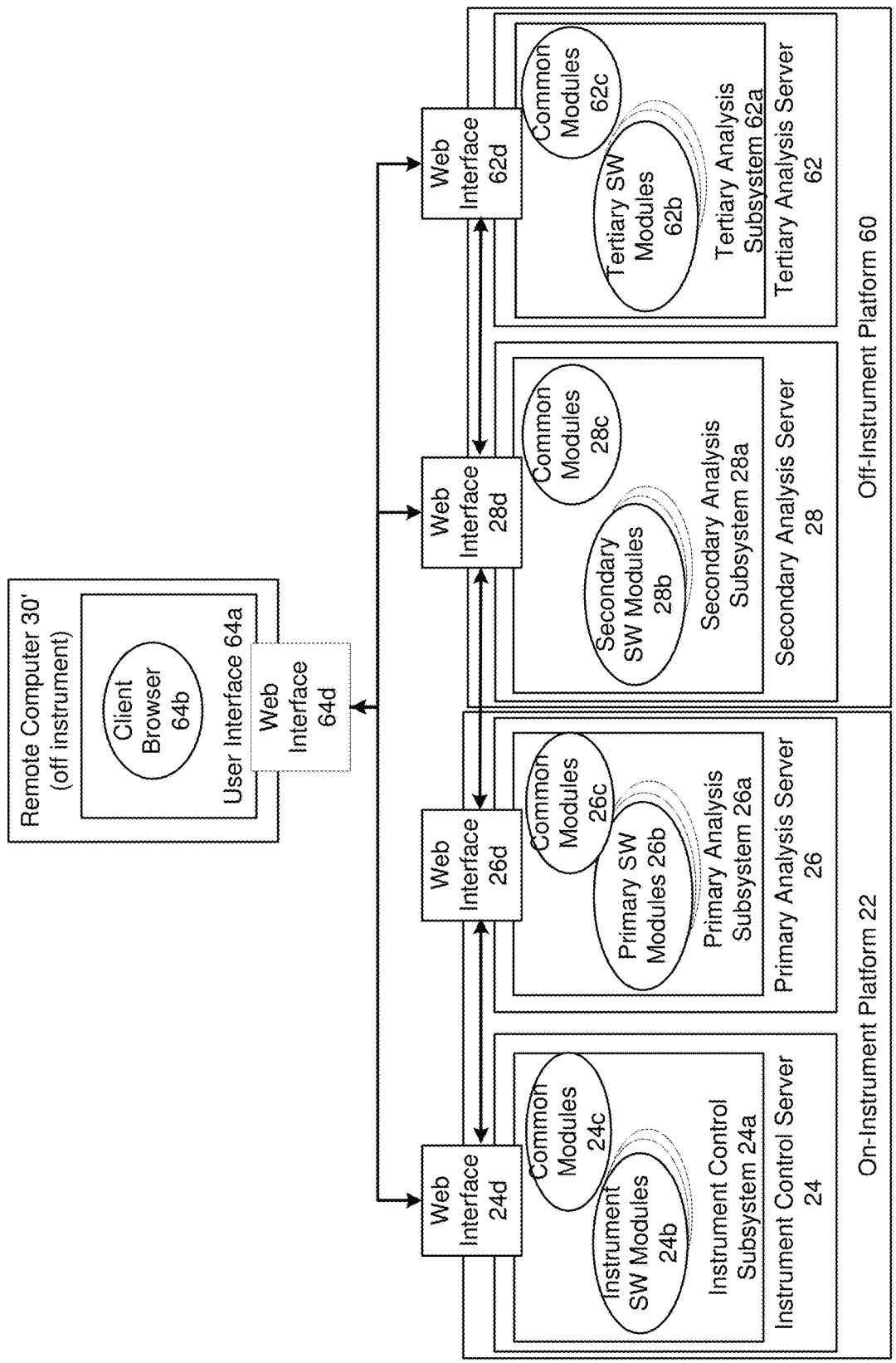
FIG. 3 is a diagram illustrating a high-level view of the subsystem software components of the multiprocessor pipeline architecture.

FIG. 3 is a diagram illustrating a high-level view of the subsystem software components of the multiprocessor pipeline architecture, where like reference numerals shown in FIG. 1A have like components. As described above, the on-instrument platform 22 may include instrument control server 24 and the primary analysis server 26, while an off-instrument platform 60 may include a secondary analysis server 28 and/or a tertiary analysis server 62. Both the on-instrument platform 22 and the off-instrument platform 60 may be controlled by the remote computer 30', which is also off-instrument.

An instrument control subsystem 24a of the instrument control server 24 comprises instrument software modules 24b, common modules 24c and a web interface 24d. A primary analysis subsystem 26a in the primary analysis server 26 comprises primary software modules 26b, common modules 26c, and a web interface 26d. A secondary analysis subsystem 28a in the secondary analysis server 28 comprises secondary software modules 28b, common modules 28c, application workflows 28e, and a web interface 28d. A tertiary analysis subsystem 62a of the tertiary analysis server 62 comprises tertiary software modules 62b, common modules 62c and a web interface 62d.

Functions of the instrument software modules 24b of the instrument control server 24a include instrument control routines for robot and environmental settings for the sequencing instrument 100. For example, the instrument control modules 24b communicates with the image sensor 123e and controls the transfer of the sensor data from the sequencing chip 120 to the IC custom coprocessor card 108. The instrument control also handles illumination source 130 control, robotic control for sample preparation, and environmental control for maintaining temperatures within the system. Instrument control settings or parameters of the instrument software modules 24b may be configured by the user interface 64a on the remote computer 30'. In one embodiment, the instrument software modules 24b may execute on the instrument control processor 102.

The primary software modules 26b refer to the primary analysis pipeline modules in the primary analysis server 26 that convert raw pixel data into base calls. The primary software modules 26b are described in further detail with respect to FIG. 4.

The secondary software modules 28b refer to secondary analysis pipeline modules in the secondary analysis server 28 that may include alignment, consensus calling and pre-assembly modules, to generate an assembled genome.

The tertiary analysis server 62 and tertiary software modules 62b may refer to any additional third-party supplied hardware and software that may be used for additional analysis of the data. The common modules 24c, 26c, 28c, and 62c handle data management for any disk drives and health monitoring of common components, such as the disk drives that are required by all subsystems. In one embodiment, the common modules 24c, 26c, 28c, and 62c may execute on the processors associated with the respective subsystems.

To provide high degree of system-wide reliability, each of the subsystems 24a, 26a, 28a, and 62a may include multiple software and hardware components to monitor and manage subsystem's health. Required hardware initialization and startup of subsystem processes may be defined in subsystem-specific configuration files, and executed at node startup by a subsystem watchdog daemon process. Once subsystem initialization completes, the watchdog process enters in subsystem monitor mode. The watchdog process constantly queries the status of configured subsystem processes, coprocessors and other hardware components, and when the watchdog process detects an anomaly, such as missing or unresponsive process, the watchdog process may attempt to correct the problem, i.e. restarting processes accordingly with their configuration. If the problem cannot be corrected, the watchdog process may restart the entire node, or perform additional diagnostics. Each of the subsystems 24a, 26a, 28a, and 62a may also include finer granularity health management services using a dedicated server component. This component may collect and store statistics at node level, from operating system and subsystem processes and services. Metrics collected and analyzed may trigger policy based actions, such as free-disk-space-threshold file delete/archive, or message-level-based user interface warning/alarm.

According to one aspect of the exemplary embodiment, each of the subsystems 24a, 26a, 28a, and 62a is provided with respective web interfaces 24a, 26a, 28a, and 62a that make the subsystems appear as a website and make the subsystems remotely accessible by the user interface 64a. The remote computer 30' includes a user interface 64a, which may be based on a client browser 64b, and a web interface 64d for controlling each of the subsystems 24a, 26a, 28a, and 62a over a network.

According to the exemplary embodiment, one added benefit of the multiprocessor pipeline scheme is that the use of remote computer user interface 64d and the respective web interfaces may enable different software modules 24b, 26b, 28b, and 62b, including the common modules 24c, 26c, 28c, and 62c and application workflows 28e, to be downloaded and/or updated. For example, a different PA custom FPGA pipeline 422 could be downloaded to the PA custom FPGA card 34' before the sequencing begins. The PA custom FPGA card 34' could also be reloaded "on-the-fly" with additional pipeline logic, if necessary, while intermediate results are maintained in memory during the chunk processing. This enables a single physical FPGA to serve as multiple pipeline steps if the total processing time allows.

Also, in the same way that the primary analysis pipeline modules can be switched, a different secondary analysis pipeline could be downloaded to the secondary analysis server 20 based on the genome size, and whether a mapped assembly (human or other known genome) or denovo assembly is to be performed. Reference genomes can be stored in non-volatile memory on the secondary analysis server 20 and updated via a wireless connection. The ability to change the secondary analysis pipeline quickly (possibly within 100 ms) enables other types of processing for specific applications beyond assembly. For example, the tertiary analysis server 62 may be provided with different downloadable "instrument application modules" for further post processing of the assembled genome. From a business perspective, the instrument control server 24, the primary analysis server 26, the secondary analysis server 28, and the tertiary analysis server 62 may be configured with specific applications and may be even priced based on those applications, while from an engineering perspective the same underlying multiprocessor pipeline architecture is utilized.

In a further embodiment, the web interfaces 24d, 26d 28d, 62d and 64d may be used to enable exchange of data using shared file systems and network communication protocols. Data availability, integrity and management are relevant and challenging, given current technologies limitations and expected average data produced and exchanged of many terabytes per day per instrument and analysis subsystems. To help provide best access performance, facilitate deployment, storage virtualization, integrity preservation, and extensible analytics and management functions, all user generated data and metadata may be stored in a different location from the core operating system, software modules and common modules. Results from acquisitions, primary analysis, secondary analysis, user protocols and more, may be organized in multiple directory structures, or branches, connected to the root of a virtual subsystem repository. Each block of resources associated with a particular entity, or store, may include metadata about content categories, service policies, list of resources, checksums, audit trail and so forth.

The software and common modules may connect to a repository by linking to the shared filesystem and communicating using the web interfaces. Transfer services provide high performance bi-directional transfer to/from filesystem, http/ftp servers, i.e. cloud, and repository-to-repository. Data management services may monitor the repository and apply user defined policies, e.g. aging based deletion/archival. Other services may be provided by external components, such as advanced search analytics.

In one embodiment, the remote computer 30' may be the same computer as the acquisition simulator server 30 of FIG. 1A, and may be an optional part of the system that is provided by a third party. In one embodiment, the acquisition simulator/remote computer 30' is capable of inputting simulated sensor data into the multiprocessor pipeline system for analysis via the serial cable (e.g. coaxial cable) 32b. This enables the multiprocessor pipeline system to process either real data or simulated data at the same frame rate produced by the sensor chip 120.

Figure 4:
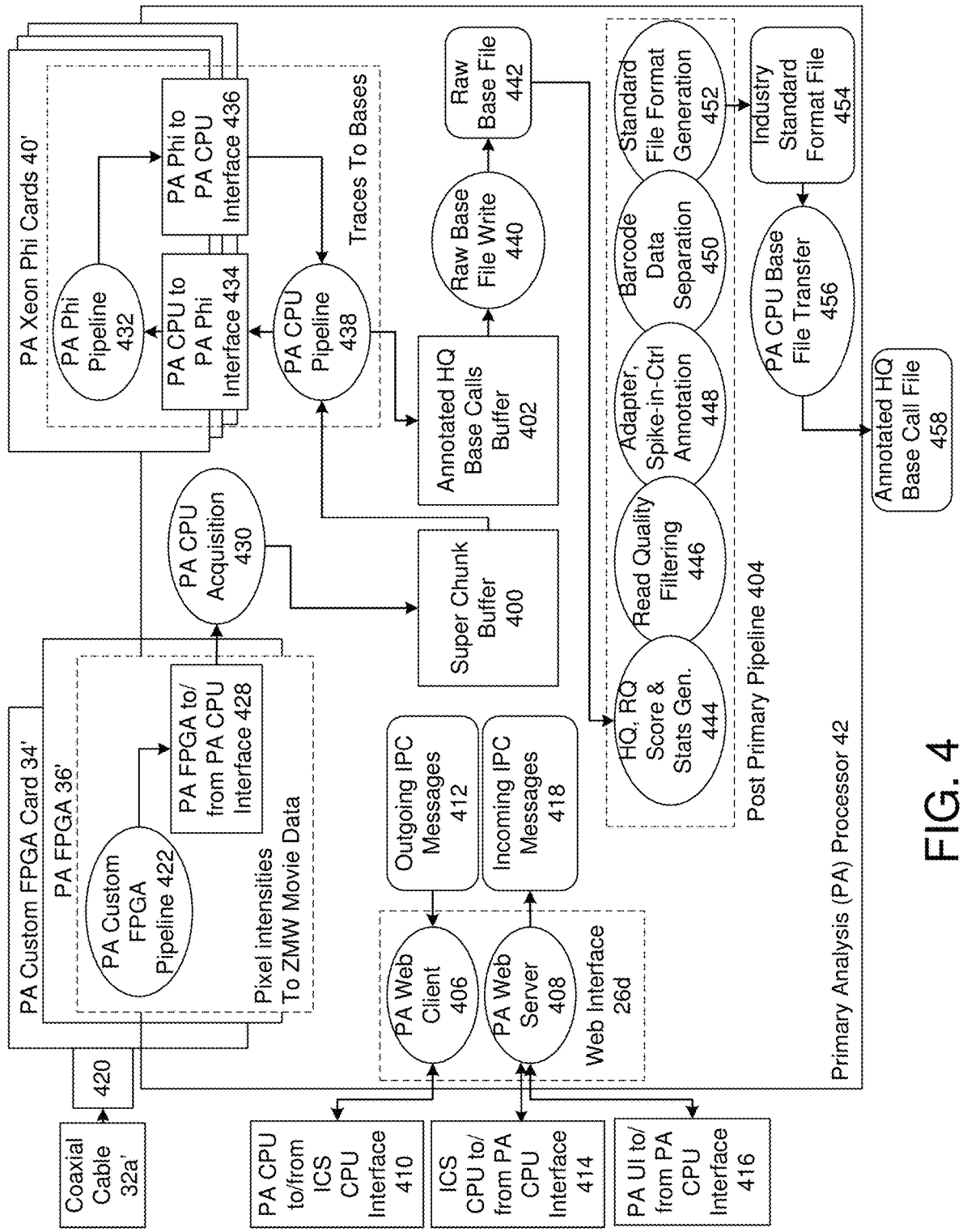
FIG. 4 is a block diagram illustrating details of the hardware, software and interface modules of the primary analysis subsystem according to one exemplary embodiment.

FIG. 4 is a block diagram illustrating details of the hardware, software and interface modules of the primary analysis subsystem 26a (FIG. 3) according to one exemplary embodiment. The primary analysis computer 42 includes the web interface 26d, global shared memory blocks shown as a super chunk buffer 400 and an annotated HQ base calls buffer 402, and a post primary pipeline 404. Oval shapes in FIG. 4 denote software modules executing in the primary analysis computer 42, the PA FPGA 36' and the PA Xeon Phi cards 40'.

The web interface 26d includes a PA web client 406 and a PA web server 408. The PA web client 406 communicates with the PA processor to/from the instrument control server (ISC) processor interface 410, and sends outgoing interprocess communication (IPC) messages 412 from executing processes. The PA web server 408 communicates with the ICS CPU to/from PA CPU Interface 414 and the PA UI to/from PA CPU Interface 416, receives incoming IPC messages 418.

The PA FPGA card 36' and the PA Xeon Phi cards 40' connect to PCIe slots in the PA processor motherboard (not shown). In one embodiment, the PA processor 42 may comprise a conventional multicore CPU having, for example, 24 cores, 512 GB of RAM, and four PCIe slots.

The PA custom FPGA card 34' is shown customized with a serial/coaxial cable connector 420 that connects the coaxial cable 32a' to the PA custom FPGA card 34'. According to one aspect of the exemplary embodiment, the serialized sensor data received via the coaxial cable 32a' flows through a real time primary analysis pipeline comprising a PA custom FPGA pipeline 422 executing in the PA FPGA 36', the super chunk buffer 400, a PA Phi pipeline 432 executing on the PA Xeon Phi cards 40', the annotated HQ base calls buffer 402, and a post primary pipeline 404 executing on the PA processor 42.

The PA custom FPGA pipeline 422 converts the pixel intensities in the serialized sensor data into reaction cell (e.g., ZMW) chunks representing movie data showing the pixel intensity values (i.e., trace signals) emitted by the respective ZMWs over time. The reaction cell chunks, which also may be referred to as ZMW movie data, are streamed out of the PA FPGA card 36' through a PA FPGA to/from PA CPU interface 428 and stored in the super chunk buffer 400 for creation of the super reaction cell chunks. Output and buffering of the super reaction cell chunks/ZMW movie data is controlled by a PA CPU acquisition module 430 executing on the PA processor 42, which may utilize direct memory access (DMA).

A PA CPU pipeline module 438 executing on the PA processor 42 coordinates the transfer of the super reaction cell chunks from the super chunked buffer 400 to the PA Phi pipelines 432 executing on the PA Xeon Phi cards 40'. The reaction cell chunks pass through a PA CPU to PA Phi interface 434 on the way to the PA Xeon Phi cards 40'.

The PA Phi pipeline 432 performs stream processing that converts the super reaction cell chunks/ZMW movie data into annotated high-quality (HQ) base calls, which are stored in annotated HQ base calls buffer 402 by the PA CPU pipeline 438. In one embodiment, for example, there may be 120 copies of the PA Phi pipeline 432 running simultaneously on each of the PA Xeon Phi cards 40'. The annotated HQ base calls are stored in annotated HQ base calls buffer 402 until all the sensor data from sample acquisition for one super reaction cell chunk delta of time has been processed. The entire pipeline processing up to this point occurs in real time at least at 100 frames per second or 450 MB per second of incoming pixel data. In one embodiment, the PA CPU acquisition module 430 and the PA CPU pipeline module 438 may be implemented as the same multithreaded component.

In one embodiment, both the super chunk buffer 400 and annotated HQ base calls buffer 402 are implemented as a portion of the memory of the PA processor 42 that is set aside as a temporary holding place for data shared by modules that operate at different speeds or with different sets of priorities.

Once all the annotated HQ base calls for one super reaction cell chunk time window have been created and stored, the raw base file write process 440 writes the data to disk as a raw base file 442, which is in a customized format. In one embodiment, the raw base file 442 may be stored in a proprietary format that is designed for the efficiency for the writing of data as fast as possible.

Once the raw base file 442 is closed, the file is processed by the post primary pipeline 404 executing on the PA processor 42. The post primary pipeline 42 comprises software modules that operate on the raw base file 442 to create a standard format annotated HQ raw base file 458. During with the execution of the post primary pipeline 42 another sample acquisition begins that is processed by the real-time primary analysis pipeline for creation of a new raw base file, while the current raw base file 442 is processed during post processing.

The software modules may include any of an HQ, RQ score & statistics generation module 444, a read quality filtering module 446, an adapter spike-in-control annotation module 448, a barcode data separation module 450, and a standard file format generation module 452 and a PA CPU base file transfer module 456. The annotated high-quality raw base calls generated by the post primary pipeline 404 are written out by the standard file format generation module 452 as an industry standard format file 454. The PA CPU base file transfer module 456 executing on the PA processor 42 completes the process by writing the annotated HQ raw base file 458 to disk. The completed annotated HQ raw base file 458 may be then output from the PA analysis server 26 to the secondary analysis server 28 for secondary base processing.

Figure 5A:
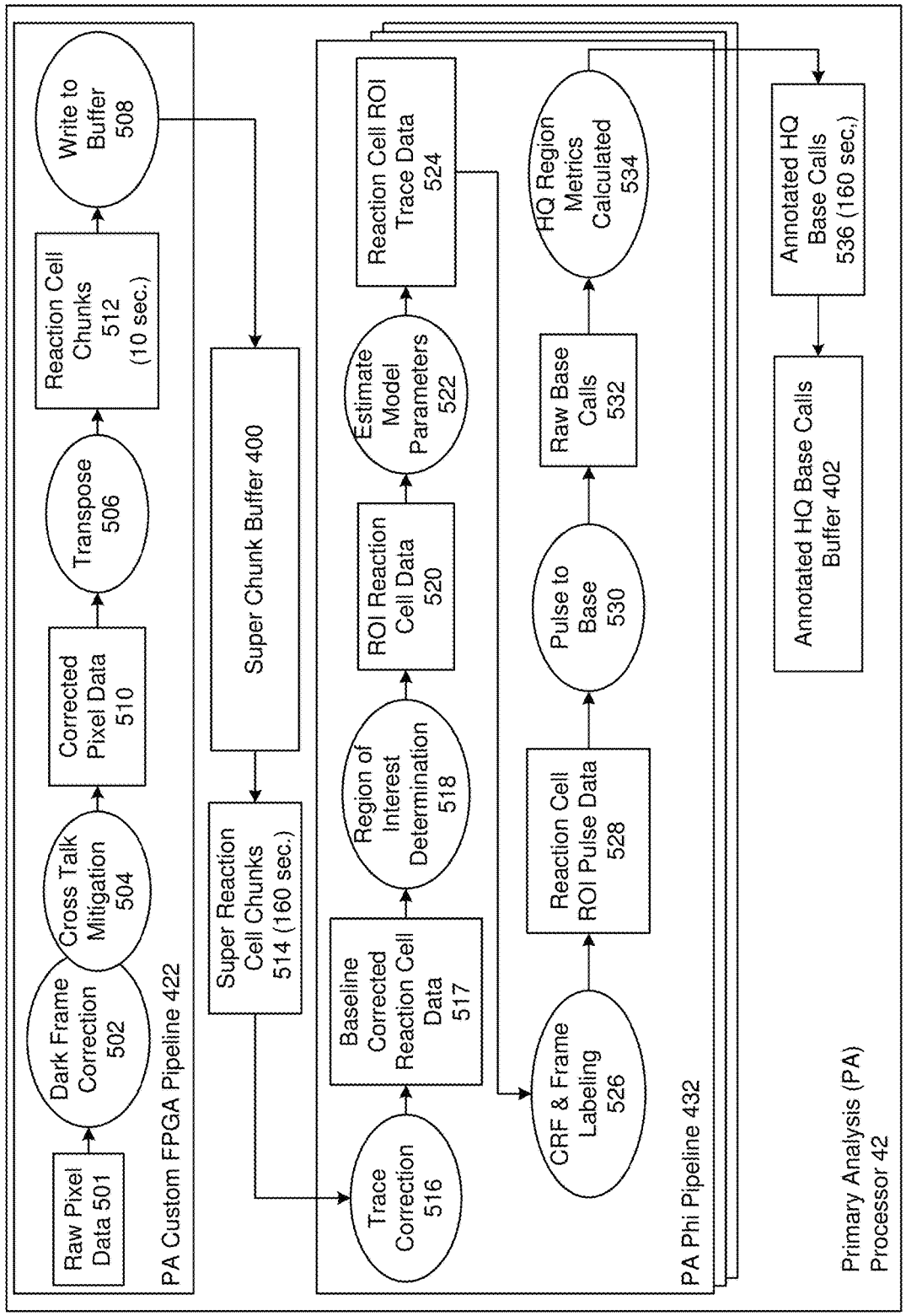
Figure 5B:
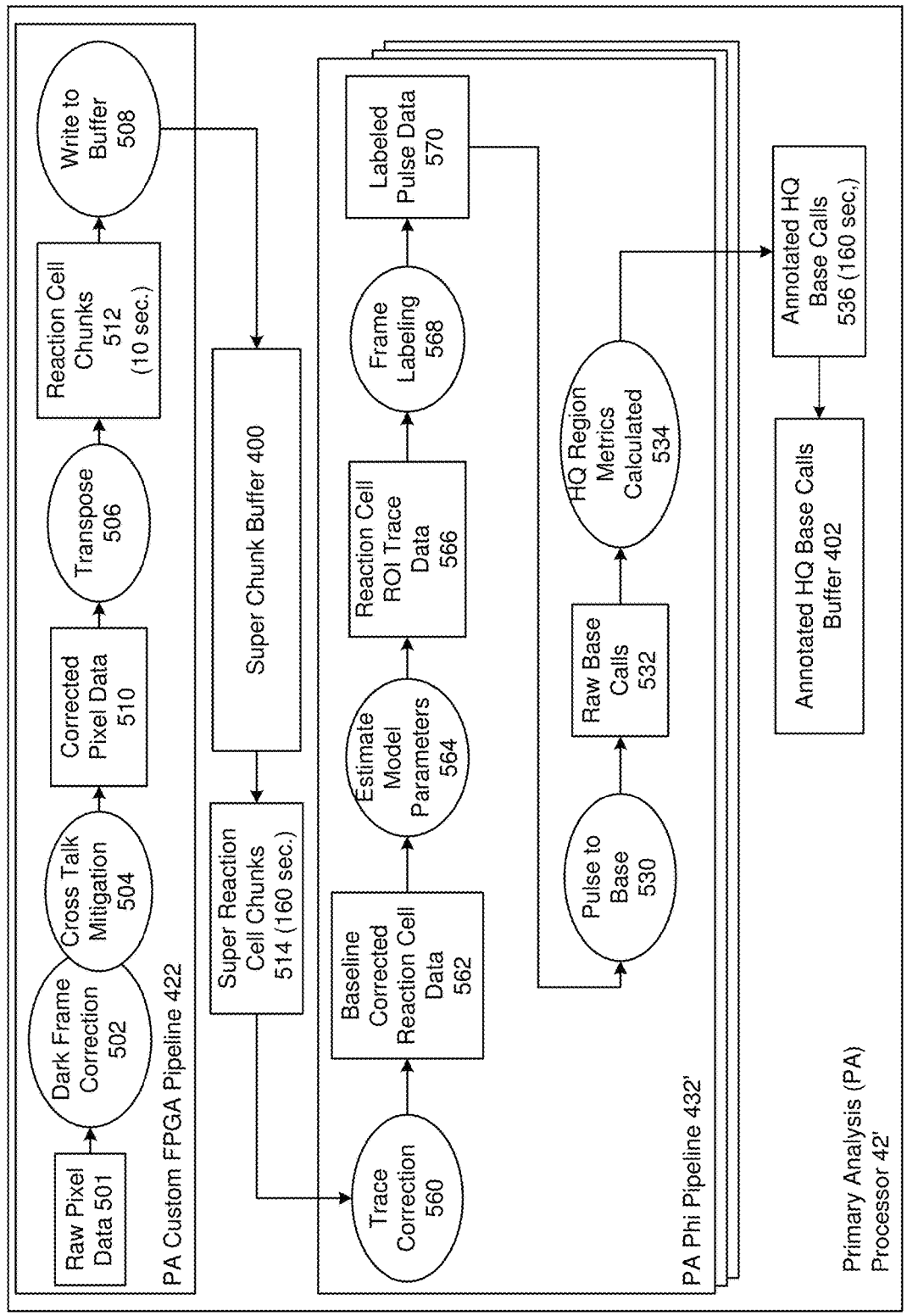

FIGS. 5A, 5B and 5C are block diagrams illustrating in further detail the processing performed by the primary analysis pipeline 500. Oval shapes in FIGS. 5A, 5B and 5C denote executing software modules, square shapes represent data, and squares with rounded corners represent files and messages.

According to one embodiment, the primary analysis pipeline 500 includes the PA custom FPGA pipeline 422 executing on the PA FPGA Card 36', the PA Phi pipeline 432 executing on the PA Xenon Phi cards 40', and the post primary pipeline 404 executing on the PA processor 42.

PA Custom FPGA Pipeline Processing

Referring to FIG. 5A, processing begins with the PA Custom FPGA Pipeline 422, which may include a dark/screen frame correction module 502, a cross talk mitigation module 504, a transpose module 506 and a write to buffer module 508. The PA Custom FPGA Pipeline 422 receives the sensor data from the sequencing instrument 100 as frames of raw pixel data 501. In one embodiment, 100 frames/sec are received where each frame comprises approximately 2 million pixels at 12 bits per/pixel.

The first step is for the dark frame and gain correction module 502 to perform dark frame and gain correction. Because the sequencing chip 120 includes an integrated image sensor 123e and is disposable after each sample acquisition, the image sensor 123e of each sequencing chip 120 has slightly different characteristics. Therefore, prior to receiving the stream of sensor data, the dark frame and gain correction module 502 first performs an image sensor calibration to determine pixel values for a dark frame output by the image sensor in absence of any input lighting. That dark frame is then subtracted from all input frames. The dark frame and gain correction module 502 also performs a gain to remove any gain applied to the frames during image capture.

Once the dark frame and gain correction module is performed, the cross talk mitigation module 504 performs cross talk mitigation to mitigate any electronic bleed of light between pixels produced by the image sensor 123e by subtracting any such bleeding light from the pixels. In one embodiment, the cross talk mitigation may utilize at least one of generalized least squares and first or second-order inverse approximation.

The dark frame and gain correction and cross talk mitigation occur in real time on the PA custom FPGA card 34'. The result is corrected pixel data 510 at a rate of 100 frames per second. As a more specific example, the corrected pixel data 510 comprise 2.07 MP frames output at 100 fps, 16 bits/pixel (415 Mbytes/sec).

The corrected pixel data 510 is then processed by the transpose module 506. The raw pixel data 500 is originally input such that the frames are stored in consecutive memory addresses in pixel order, which is spatially based (The light emitted by each reaction cell/ZMW 123b is represented by the same set of pixels (e.g. 2 pixels) in each frame). However, downstream processing requires the intensity values for each set of pixels to be stored in memory ordered in time.

According to one aspect of the exemplary embodiment, the transpose module 506 gathers the intensity values for each set of pixels through the frames for each reaction cell 123b/ZMW over a predetermined time window. The transposition process 506 then transposes or rearranges the pixel data so that the intensity values of the pixels assigned to a particular reaction cell 123b are stored in a set of consecutive memory addresses, referred to herein as reaction cell chunks 512. Each of the reaction cell chunks 512 thus represent movie data showing the pixel intensity values (i.e., trace signals) emitted by a respective reaction cell/ZMW over a predetermined time window. In one embodiment, the predetermined time window may be 5-50 seconds, for example. Stated differently, the transpose module 506 buffers some number of images/frames in FPGA memory over a predetermined time, such as 10 seconds, and then transposes the pixel data so that that the intensity values for a particular set of pixels at time/frame T1/F1, T2/F2, . . . T10/F10, are stored in a set of consecutive memory addresses. Consequently, the transpose process converts the spatial data of the frames into time data in consecutive memory addresses. In one embodiment, the value for the time window during which the images/frames are buffered depends upon the amount of onboard memory available on the PA custom FPGA card 34'.

The transpose process results in reaction cell chunks 512 that are a predetermined time window in length, e.g., 10 seconds. In one embodiment, the reaction cell chunks 512 comprise data for 2.74 M pixels at 100 fps (4 bytes/ZMW or 415 Mbytes/sec). A write to buffer module 508 writes each of the reaction cell chunks 512 to the super chunk buffer 400 in the primary analysis server 26.

The purpose of the super chunk buffer 400 is to store or buffer the reaction cell chunks 512 for each respective reaction cell 123b over a larger predetermined time window so that larger super reaction cell chunks 514 can be created and streamed to the PA Phi pipeline 432. In one embodiment, the larger predetermined time window may be 120-160 seconds, for example, creating super reaction cell chunks 514 that are approximately 120-160 seconds in length. Thus, in one embodiment, the 10 second stream size reaction cell chunks 512 are staged in the super chunk buffer 400 in order to build up a 160 seconds stream size/time window in which the intensity values over 160 seconds for each set of pixels are stored in consecutive memory locations. The reason for the buffering is that the PA custom FPGA card 34' is limited to a memory capacity sufficient to store only 10 to 20 seconds worth of intensity values. In an embodiment where the custom FPGA card 34' has sufficient memory resources, the reaction cell chunks 512 could be stored directly as super reaction cell chunks 514.

Once the super reaction cell chunks 514 are ready, the PA CPU Pipeline 438 streams the super reaction cell chunks 514 from the super chunk buffer 400 to the PA Phi pipeline 432 in the PA Xeon Phi cards 40'. Simultaneously, the PA FPGA pipeline 422 processes fills the super chunk buffer 400 with the next 120-160 seconds of reaction cell chunks 512 to create the next super reaction cell chunk 514.

In one embodiment, the super chunk buffer 400 may be implemented as a ping-pong buffer in which the 120-160 second super reaction cell chunks 514 are parsed out in contiguous smaller chunks to the PA Xeon Phi Cards 40' as needed, while the data for another super reaction cell chunk 514 is buffered. However, once a smaller chunk is passed to a particular PA Xeon Phi card 40', there's no guarantee that the smaller chunk will be processed at the same speed as smaller chunks in the other PA Xeon Phi cards 40's.

In accordance with a further embodiment, the super chunk buffer 400 may be partitioned into a set of data tiles or tranches. For example, the super chunk buffer 400 may be partitioned into approximately 16 data tiles or tranches. As the data tiles are filled with reaction cell chunks 512, the data tiles are passed in order to the PA Xeon Phi cards 40' as Phi cards 40' become available. As soon as a tile/tranche of the super chunk buffer 400 is freed up, that data tile is used to store additional reaction cell chunks 512. This allows greater flexibility for memory management and allows the PA FPGA pipeline 422 to be more tolerant of downstream processing delays in the PA Xeon Phi cards 40'.

In one embodiment the PA CPU acquisition process 430 and the PA CPU pipeline process 438 may use metadata indexing to keep track of the order that the data tiles are output, as well as which emptied data tiles are available for use next. The metadata indexing information is fed to the PA custom FPGA card 34' to inform it where to store the next reaction cell chunk 512. In one embodiment, IPC messaging may be used to send the metadata indexing information between processes.

PA Phi Pipeline Processing

The PA Xeon Phi cards 40' may each include, for example, a 48 or 60 logical core vector processor (compared with 12 or 24 cores in the primary analysis CPU) with multiple threads in each core, resulting in upwards of 120-180 copies of the PA Phi pipeline 432 executing in each core. A vector processor implements an instruction set containing instructions that operate on one-dimensional arrays of data called vectors. Common examples of vector architectures include VIS, MMX, SSE, AltiVec and AVX.

Now that the super reaction cell chunks 514 are aligned in 120-160 seconds chunks of time, the data is structured as vector of data whose width is aligned with the vector processing capability of the PA Xeon Phi cards 40'. This enables the data to be pushed through the pipeline to efficiently using vector processing to the fullest.

The first level of processing performed by a trace correction module 516 is baseline estimation and subtraction. With digital data, it would be desirable if the signal traces represented in the super reaction cell chunks 514 were represented with perfect square waves that ride over a baseline of light values. The reality is that the baseline is wavy over time. The trace correction module 516 identifies that baseline value so that the trace signals can be normalized to a set of traces with heights that are detectable. The output is corrected signal traces referred to as baseline corrected reaction cell data 517. In one embodiment, the baseline corrected reaction cell data 516 comprises 1.04 M pixels at 100 fps, 4 bytes/ZMW. In this embodiment, the baseline corrected reaction cell data 516 is still 2-channel data, i.e. two pixels per reaction cell/ZMW, each pixel representing a color, where the signal traces represent a pixel value over time at hundred frames per second (due to the image sensor being aligned with the ZMW poles. Two pixels can be used to detect four bases where the four base colors are distinguished by amplitude of the signal traces, each pixel can detect two colors using two different amplitudes, low and high, as shown in FIG. 1C.

Next, region of interest (ROI) determination is performed by a region of interest determination module 518. Given the baseline corrected reaction cell data 517, the region of interest determination module 518 determines locations of the signal traces along the data so that the signal traces are processed. The region of interest determination module 518 outputs only those locations or region of interest as ROI reaction cell data 520.

The estimate model parameters module 522 estimates model parameters. As stated above, the analysis region 123 of the sequencing chip 120 is disposable after each use. Therefore, the image sensor 123e of each analysis region 123 must be calibrated for each new image sensor's characteristics. The first calibration performed is the dark frame/grain frame calibration performed by PA custom FPGA pipeline 422 before acquisition begins. The second calibration is performed by the estimate model parameters module 522 using a spectral matrix that determines how particular colors show up on each of the set of pixels assigned to each reaction cell 123b. In the two pixel implementation, each pixel is supposed to detect a unique a color based on the way the filter stack and the optical stack is configured inside the sequencing chip 120. The optical stack is designed to split the light emitted from the reaction cell 123b so that one color goes to one pixel and another color goes to the second pixel. In reality, all the alignments of all the filters and lenses and reaction cell in each optical stack are different so the splitting of light occurs in slightly different arrangements. Therefore the color matrix must be calibrated for each reaction cell 123b. Over time the colors for each reaction cell 123b are calibrated as part of the real-time processing that is performed by the estimate model parameters module 522. The result is reaction cell ROI trace data 524 along with parameters. In one embodiment, the reaction cell ROI trace data 524 may comprise 1.04 M pixels, 3 parameters/trace at 8 traces/sec (440 Mbytes/sec).

Once the reaction cell ROI trace data 524 is obtained, the data is processed through a conditional random field (CRF) algorithm and frame labeling module 526, which is configured to label each trace event. This step of the Phi pipeline 432 processing converts trace data to pulse data and assigns to each of the pulses a base label (A, T, C, G). Since trace data may operate at 100 hundred frames per second and pulse data may operate on average at 3 to 5 bases per second, this processing results in significant data reduction. The result is reaction cell ROI trace data 528 with assigned frame labels (if applicable) and parameters (e.g., 1.04 pixels (465 Mbytes/sec)).

The pulse to base module 530 examines other characteristics and context to determine whether each assigned frame label is correct, e.g. an event labeled "A" is deemed "AA". This process uses data including inter-pulse distance, pulse width, and PK-mid value (average signal height) to make this determination. The pulse to base module 530 may also uses machine learning concepts in which the algorithm is trained with historical data to recognize characteristics and events. Quality/confidence values are also assigned to the assigned frame labels based on the characteristics of the signal pulses. The pulse to base module 530 outputs raw base calls 532 or read sequence (e.g., 1.04 million pixels (66 Mbytes/second)).

The high-quality (HQ) region metrics module 534 calculates metrics that are used downstream in the post primary pipeline 404 (FIG. 5B) to determine what part of the raw base calls 532/read sequence will be identified as high quality. One metric would be the pulse rate. If the data shows a very high pulse rate then transitions to a more regular pulse rate, then the high pulse rate may be indicative of two polymerase being present in the same reaction cell 123b, and only the reads for the regular pulse rate would be considered high quality. The (HQ) region metrics module 534 outputs annotated HQ base calls 536.

The annotated HQ base calls 536 are stored in the annotated HQ base calls buffer 402. In one embodiment, the annotated HQ base calls are stored in 120-160 second blocks and annotated with metric calculations that may include metrics and base width and/or whole chunk metrics. Example types of metrics associated with the base call may include, start, width, PKmid, PKMax, and quality values (QVs). Example types of whole chunk metrics may include average base rate and average SNR detected that affect the quality of the data. In one specific embodiment, the annotated HQ base calls 536 may comprise 1.04 M pixels, ~4 Bases/sec, Base call, Start, Width, PKmid, PKmax, QVs, and 1 minute blocks (66 Mbytes/sec).

In the case of human genome sequencing, the primary analysis pipeline may execute for approximately three hours for each sample acquisition and generate approximately 200 GB of annotated HQ base calls 536, which are stored in the annotated HQ base calls buffer 402.

It should be noted that the PA custom FPGA pipeline 422 results in reaction cell chunks 512 of a predetermined time window, e.g., 10 seconds, and therefore has a stream processing size of approximately 10 seconds, while the PA Phi pipeline 432 operates on super reaction cell chunks 514 of a larger predetermined time window, e.g., 120-160 seconds, and therefore has a time window or stream size of approximately 120-160 seconds.

PA Custom FPGA Pipeline Processing—Single Instruction, Multiple Reaction-Cell Data Processing FIG. 5B is a block diagram illustrating an alternative embodiment of the primary analysis Phi pipeline 432' of the primary analysis pipeline 500'. This embodiment provides a process for single instruction, multiple reaction-cell data processing for primary feature-finding and identification (base calling) for supporting sequencing instrument 100 or other types of single-molecule, real-time detection devices.

As described above, high multiplex, single-molecule real-time detection devices, including sequencing instrument 100, typically read out the detection signals that record the activity of multiple reaction cells (ZMWs, nanopores, etc.) simultaneously, each corresponding to a single molecular experiment of interest (e.g., an enzyme complex performing a sequencing reaction on a DNA template molecule). Examples of such detection signals include the readout of a voltage from a photo-electric device such as a CCD or CMOS sensor (where the voltage typically derives from an intensity of optical emission in a selected wavelength band that identifies or quantifies a chemical label associated with the experiment), or the readout of a voltage or current that is otherwise derived electronically from molecular activity associated with the experiment (such as the modulation of current due to the passage of a molecular component such as a nucleic acid molecule or labeled nucleotide of the experiment through a biological or synthetic nanopore associated with the detection apparatus, or the modulation of the current at the gate of a nanoscale field effect transducer (nanoFET)).

Computer codes for processing real-time trace data that encodes single-molecule activity are typically written to process one reaction, or experiment, at a time. Or, on multi-core/multi-threaded hardware, may achieve parallelism (increased speed or throughput) by processing one experiment or portion of an experiment serially per thread of execution, but using multiple threads simultaneously.

To achieve additional performance gains, vector processing may be used. A vector processor or array processor is a processor that implements an instruction set containing instructions that operate on one-dimensional arrays of data called vectors, compared to scalar processors, whose instructions operate on single data items. Examples of such instruction sets include Single Instruction Multiple Data (SIMD) and Multiple Instruction, Multiple Data (MIMD).

Traditional primary analysis codes, or algorithms, generally use vector processing to take advantage of data parallel opportunities within the processing steps that involve the analysis of the data for a single experiment. For example, a conventional approach may structure the code to "vectorize" large loops over the time-series samples (i.e., a trace) that correspond to the data collected for a single experiment. The problem with this approach is that either (1) the program or programmer must rely on the compiler to automatically perform the SIMD/vector optimization, or (2) the program must include custom, low-level programming instructions, which are generally of a different or unique nature for each of the algorithm sub-routines. For example, in a 4-color system, computer codes written for vector processing hardware that has vector width N=4 might best take advantage of this in specific sub-routines via explicit SIMD instructions that process the 4 channels simultaneously.

With either approach, it is difficult to take full advantage of the processor's vector processing capabilities, leading to a loss of efficiency in the software vs. the full hardware capabilities. Secondly, as hardware vendors increase the width of the SIMD or vector units (e.g., from N=16 to N=32), codes will, in some cases, have to be significantly re-designed or re-structured, depending on the details of the algorithmic approach or degree of optimization required.

The present embodiment solves this problem by implementing algorithms used, for example, for single-molecule experiment analyses, such as the primary analysis Phi pipeline 432' executed by the PA coprocessors 40, to be completely, or nearly completely, data-parallel over all or substantially all reaction cells. The present embodiment implements the primary analysis Phi pipeline 432' so that a time-series analysis for N independent sequencing reactions is performed simultaneously on an algorithm thread using vector processing of the PA coprocessors 40 (and/or the PA processor 42). In the present embodiment, rather than utilizing the vector processing units to process only portions of a single experiment or trace, the present embodiment utilizes vector processing units throughout the primary analysis Phi pipeline 432' steps to analyze multiple, independent experiments or traces simultaneously.

For example, the sequencing chip 100 includes a single polymerase per reaction cell 123b, so there is one sequencing reaction for each reaction cell 123b. If each PA coprocessor 40 includes C logical cores, and each logical core utilizes a SIMD register having N dimensions or slots, where each slot processes one independent sequencing reaction for a reaction cell (or trace analysis problem), then the total parallelism or independent reactions E processed simultaneously for the C multiple cores is E=C×N. For example, if a processor provides 48 hardware threads or logical cores, and each logical core has a hardware vector width of 16, then C=48, N=16 and the number of independent reactions (E) processed in parallel is 48×16, which is 768. In this example, a 16× speed-up or equivalent increase in throughput capability is achieved over what would be achieved on standard multi-threaded hardware, using essentially equivalent algorithmic steps, e.g. as expressed in a programming language.

Referring to FIG. 5B, data parallel components of the PA Phi pipeline 432' may implemented by first providing data structures that satisfy all, or substantially all, low-level mathematical operations that are typically used on scalar data elements (e.g., integer or floating-point representations) that contain data for N values, each of which belongs to one independent sequencing reaction or trace. In these data structures, the N independent values are packed in such a way that the low-level mathematical operations (for example, floating-point multiplication) occur for all N values simultaneously via the hardware vector processing units, in the same number of cycles that would typically be used for a scalar equivalent operation.

Second, components of the PA Phi pipeline 432' may implemented by providing a structure of the PA Phi pipeline 432' algorithms that is completely, or substantially completely, data parallel, by, for example, performing the same set of algorithmic steps on each corresponding data element of the N sequencing reactions, unconditionally. This design avoids algorithms that require branching, e.g., "do steps (A, B) if a data value is below some threshold, but do steps (C, D, E) if it is greater or equal to the threshold," where the data value might be an intensity measured in a pixel or color channel at time T, for example. Since each reaction will record a distinct, independent value at a given time, the steps performed for the two cases with code that requires branching may be different, and such an algorithm design is therefore not data parallel.

In one embodiment, the data parallel components of the PA phi pipeline 432' may include trace correction module 560, estimate model parameters module 564, and frame labeling module 568. The trace correction module 560 identifies a baseline value so that the trace signals can be normalized to a set of traces with heights that are detectable. The output is corrected signal traces referred to as baseline corrected reaction cell data 562. Suitable data parallel algorithms used during trace correction may include, for example, parameter estimation algorithms, including morphological filters for estimating background distribution and smoothing filters (FIR or IIR), e.g., contributing to estimation of background distribution.

The estimate model parameters module 522 estimates model parameters using the baseline corrected reaction cell data 562 to calibrate the color matrix for each reaction cell 123*b*. The result is reaction cell ROI trace data 566 along with parameters. Suitable data parallel algorithms used by the estimate model parameters module 522 may include smoothing filters and mixture-model algorithms, e.g., expectation/maximization (EM) for estimating the parameters of analog intensity vs. spectral bin mode distributions.

Once the reaction cell ROI trace data 562 is obtained, the data is processed through a frame labeling module 560, which is configured to label each trace event by converting trace data to pulse data and assigning to each of the pulses a base label (A, T, C, G). The result is labeled pulse events and parameters 570. Suitable data parallel algorithms for pulse identification used by the frame labeling module 560 may include, for example, detection/classification algorithms using a dynamic programming strategy, including (a) the Viterbi algorithm, for finding the most likely sequence of hidden states using a Hidden Markov Model (HMM); and/or (b) the Viterbi algorithm, for finding the most likely sequence of hidden states using a Conditional Random Field (CRF) model.

Post Primary Pipeline Processing

FIG. 5C is a block diagram illustrating process is performed by the post primary pipeline 404 stage of the primary analysis pipeline 500, 500'. One purpose of the post primary pipeline processing is to convert raw base calls into annotated high-quality (HQ) base calls, which are stored in an industry-standard base call file 458 suitable for transference to secondary analysis.

Once acquisition of the sequence chip 100 is finished and storage of the annotated HQ base calls 536 in the annotated HQ base calls buffer 402 completes, the real-time process is complete and the post primary pipeline 404 begins. The post primary pipeline 404 processes the entire movie of base calls or raw reads too high-quality and barcode annotated base calls that are stored in an industry standard format (e.g., BAM format).

The post primary pipeline processing begins by a parallel file writer module 538 writing the buffered annotated HQ base calls 536 to disk as a raw reads file 540 with metrics. In one embodiment, the raw reads file 540 may be stored, for example, a file format designed for the efficient (and fast) writing of data to disk. For example, in one specific embodiment, a proprietary format called BAZ may be used. Other formats are also suitable. As stated above, in one example implementation, one acquisition of the sequencing chip 100 results in one raw reads file 540 over approximately three hours. As soon as the sequencing chip 100 is set for another acquisition, additional annotated HQ base calls 536 will be processed and stored in the annotated HQ base calls buffer 402 to create a new raw reads file 540 at the same time as the current raw reads file 540 is processed by the post primary pipeline 404. This keeps the duty cycle of the multiprocessor pipeline running at full capacity. To produce a gold standard human genome sequence, for instance, 12 sequencing chips may be required, resulting in 12 three-hour movies, and 12 raw reads files 540.

The post primary pipeline 404 performs high-quality identification, adapter, spike-in-control, an optionally barcode data separation. The HQ, RQ (Read quality) score and statistics generation module 444 identifies and annotates high-quality (HQ) regions in the raw reads file 540. Recall that the reaction cells 123*b* on the sequencing chip 120 hold sample fragments. Quality assignment may be based on high-quality identifications, which are based on quality values assigned to the bases within each high-quality region; and the process then assigns a read quality to the entire DNA read of each fragment. The output is HQ annotated and RQ scored reads 544.

The read quality filtering module 446 determines which of the HQ annotated and RQ scored reads 544 satisfy a certain quality of performance by examining upstream calculated metrics produced by the primary analysis pipeline. The read quality filtering module 446 determines, given those metrics applied to chunks of the reads, which parts of the reads are considered sufficiently high quality to pass through to the remainder of the post primary pipeline 404 to prevent bad reads from propagating through the system. The result is filtered reads 546.

In one embodiment, the sample fragments held by the reaction cells 123*b* may be in what is known as a smart bell structure, which is a continuous loop of DNA and the DNA of interest are templates in the middle of the loop. The sequence process actually sequences around the loop multiple times. The adapter identification and spike-in-control annotation module 448 identifies the adapter sequence locations on the end of the loop to locate the specific sequences of interest to retain the DNA template information. During the sample preparation process, the sample fragments may be optionally provided with additional spiked-in samples that are not part of the sample fragments being sequenced to gauge overall success of the sequencing process. The adapter identification and spike-in-control annotation module 448 also identifies and separates out those spiked-in samples from the filtered reads file 546. The result is subreads file 548, which in one embodiment, may comprise an approximately a 20,000 long base read representing multiple sequences around the loop or smart bell structure in the reaction cells 123*b*.

An optional barcode processing path 458 may be used to process any barcode data present in the subreads file 548. Because of the throughput of the sequencing chip 120 is so great, multiple samples/experiments can be run on a single chip 120. During the sample preparation process, a DNA barcode may be placed on the samples that are part of the same experiment. For example assume there are 20 different microbes being sequenced. The samples from each microbe are given a common barcode identifier.

A barcode data separation module 450 finds the barcodes applied to the samples and separates read groups based on barcode identification. The output is a barcode separated data file 550 having annotations for the different barcode sections. In another embodiment, different barcode separated data files 550 may be created corresponding to the different samples.

The standard file format generation module 452 converts either the subreads file 548 or the optional barcode separated data file(s) 550 into an annotated HQ base call file 458 in an industry standard file format, such as BAM, FastQ, or the like. When data processing completes and the annotated HQ base call file 458 is closed, the annotated HQ base call file 458 is ready to be transferred (block 522) off the primary analysis server 26 to the secondary analysis server 28 for secondary analysis processing. In one embodiment, the annotated HQ base call file 458 may be transferred through immediate streaming to the secondary analysis server 28. In an alternative embodiment, the annotated HQ base call file 458 may be copied to the secondary analysis server 28.

According to one aspect of the exemplary embodiment, the primary analysis pipeline described in FIGS. 5A and 5B performs stream processing in which various pipeline stages have increasingly larger time windows of stream processing. For example, starting with the beginning of the PA custom FPGA pipeline 422, the sensor data is input at 100 frames per second. The dark/grain frame correction module 502 and the cross talk mitigation module 504 operate on one frame of sensor data at a time, meaning these processes have is a time window or stream size of approximately 10 ms. The time window or stream size for the transpose module 506, however, is approximately 10 seconds, while the time window or stream size for the super chunk buffer 400 and the trace correction module 514 is approximately 120-160 seconds.

The post primary pipeline 404 must wait for an entire acquisition to complete and after raw read file 540 is written to disk 542, which may be about three hours' worth of data. Therefore, the time window or stream size of the post primary pipeline 404 is approximately three hours. As can be seen, the stream time windows become progressively larger as the pipeline processing progresses. Stated another way, the super chunk buffer 400 and the annotated HQ base calls buffer 402 are 120-160 second buffers, whereas the post primary pipeline 404 can be considered a three-hour buffer. According to another aspect of the exemplary embodiment, the time windows or stream sizes of the pipeline processes and buffers are configurable based on the application and hardware resources available.

Secondary Analysis

Figure 6:
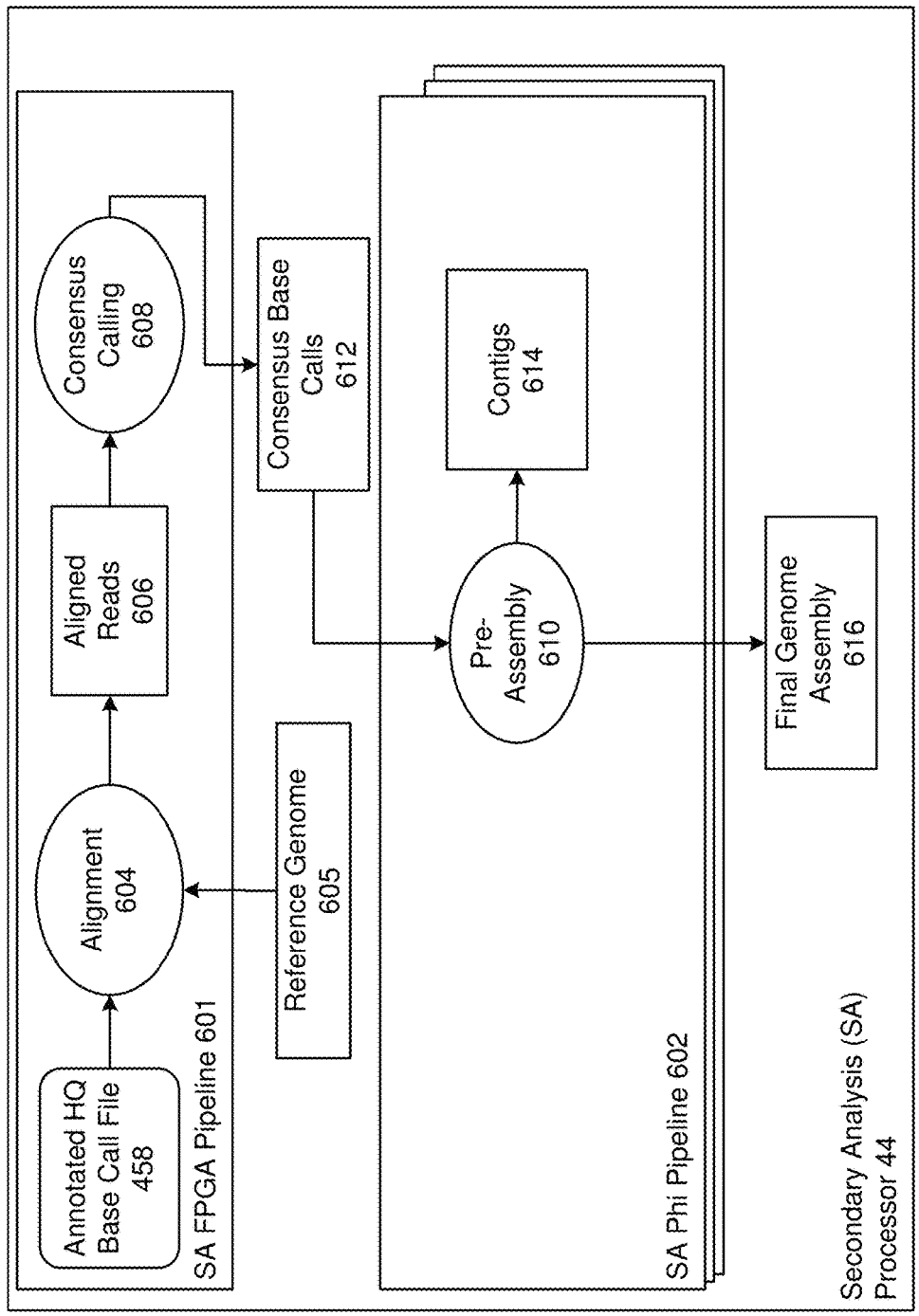
FIG. 6 is a diagram illustrating the processing performed secondary analysis pipeline in the secondary analysis server.

FIG. 6 is a diagram illustrating the processing performed secondary analysis pipeline 600 in the secondary analysis server 28. According to one embodiment, the secondary analysis pipeline 600 includes a SA FPGA pipeline 601 executing on a SA coprocessor (e.g., the SA FPGA card 48) and a SA Phi pipeline 602 executing on a plurality of other SA coprocessors (e.g., the SA Xenon Phi cards 46). The secondary analysis pipeline 600 may include an alignment module 604, consensus calling module 606 and an assembly module 610, collectively referred to as final assembly modules.

As is well known in the art, alignment is an iterative process by which related reads, i.e., sequences of base calls, are aligned to each other or to a reference based on overlapping of the reads, resulting in many overlapping reads. This is followed by consensus base calling, which given all the overlapping reads, calculates the order of the most frequent base calls at each location of the reads and forms a consensus on the base calls, which is called a consensus sequence. Once many overlapping reads are identified and consensus called reads formed, assembly is performed on those resulting consensus called reads. Assembly aligns and merges fragments of the consensus called reads to form larger contiguous sequences, called contigs in order to reconstruct the original sequence and create an assembled genome.

In a conventional final assembly process, all the base call data is typically generated and collected first before the final assembly process can begin. Using the multiprocessor pipeline process described above, collection and generation of the base call data for the human genome may require approximately 36 hours. Assuming that a conventional final assembly process would require an additional 36 hours to complete, the entire process would not complete until 72 hours after the start of sample acquisition.

According to another aspect of the exemplary embodiments, the secondary analysis server 28 is configured to provide the necessary memory bandwidth and parallelized computational resources needed to perform the entire genome assembly from in "chunked" real time. This means that a streaming assembly process begins once a predetermined fragment read size is obtained even if there is still more data coming in the stream. In one embodiment, the predetermined fragment read size may comprise the annotated HQ base call file 458 generated on a per sequencing chip basis, rather than waiting for acquisition of the base calls generated by all 12 sequencing chips, for example.

In another embodiment, the predetermined fragment read size may comprise a number of base calls read from the annotated HQ base call file 458 sufficient to form overlaps and/or make a consensus. For example, if the sequencing chip 120 supports a 25,000 base read for the individual fragments, then the fragment read size may be designated as 1,000 bases from of the annotated HQ base call file 458.

Performing conventional final assembly for 3 billion base Human Genome with 30× coverage would could require a larger external memory block accessible by the SA FPGN 48 than required for primary analysis. However, by starting the final assembly process before all the data has arrived the total amount of memory needed will be less than that needed to hold all of the base calls and assembly data. Thus, beginning final assembly process as soon as possible after chunks of data are collected as performed by the secondary analysis pipeline reduces the latency time from the start of the experiment to the final output, as well as reduces the resources required to complete the entire job.

The secondary analysis pipeline may begin with the alignment module 604 reading the predetermined fragment read size from the annotated HQ base call file 458. The alignment module 604 may to start placing reads on a reference genome 605 or for a de novo assembly, start searching for and refining intermediate overlaps to generate an intermediate overlap graph and aligned reads 606. In one embodiment, the reference genome 605 may be stored on disk and transferred to a memory of the secondary analysis processor 44 or a memory within the SA FPGA 48. The preliminary alignment module 604 is configured to update/refine those placements or intermediate overlaps after another predetermined fragment size or chunk is read from the annotated HQ base call file 458 and so on.

The consensus calling module 608 may read the aligned reads 606, generate preliminary consensus base calls 612 for particular positions and update/refine those consensus base calls 612 for each newly received fragment read size. In one embodiment, this consensus base calls 612 may be stored in memory on the secondary analysis processor 444.

The pre-assembly module 610 may read the preliminary consensus base calls 612 and generate preliminary contigs 614. The pre-assembly module 610 may update/refine the preliminary contigs 614 for each newly received fragment read size. Once it is determined is there are no more fragments to read, the preliminary contigs may be output as the final genome assembly 616 with per base quality values and other run summary data. The resulting finished genome assembly 616 may be streamed off the instrument as soon as the last "chunk" of data is processed by the assembler.

Given this pipeline architecture from raw signals to finished assembled sequence is continuously executing as soon as the data starts streaming off the image sensor, the time to finished answer is very soon after the acquisition completes. Depending on the "time depth" of the entire FPGA pipeline it's quite possible that a finished human genome assembly could be completed within a few minutes of acquisition completion. In the example above where the fragment read size is 1000 bases, then the total time it would take to generate the final genome assembly 616 after the "acquisition" completes would be the time that it takes for the last base of the fragments to get through the primary analysis pipeline plus the time to process the last chunk (e.g. 1,000/25,000*15 minutes) which is 36 seconds.

In the example above where the fragment read size is the annotated base call file 458, then the total time it would take to generate the final genome assembly 616 after the "acquisition" of the last sequencing chip 120 (36 hours) plus the time to process the last chunk (3 hours), which is 39 hours. Thus 39 hours after starting the acquisition process for the first sequencing chip 120, the system will have a human assembly, compared to 72 hours using a conventional final assembly process.

A multiprocessor pipeline architecture has been described. In some aspects, the invention includes an article of manufacture comprising the multiprocessor pipeline architecture that includes a computer or machine-readable medium containing one or more instructions, which when executed implement the steps of the invention as described herein. The instructions may include one or more of the processes performed by the modules comprising the multiprocessor pipeline architecture described above. In certain embodiments, the computer-readable medium comprises any combination of a hard drive, internal memory auxiliary memory, external memory, server, database, portable memory device (CD-ft DVD, Blu-ray, flash memory cards, etc.), and the like.

Although the instrument control server 24, the primary analysis server 26, the secondary analysis server 28, the tertiary analysis server 62, and the remote computer 30 are shown as single computers, it should be understood that the functions of these servers may be distributed over more than one server, and the functionality of software modules may be implemented using a different number of software components. In addition, the servers may be implemented as general computers, rather than servers Furthermore, the functional aspects of the invention, as will be understood to one of ordinary skill in the art, may be implemented or accomplished using any appropriate implementation environment or programming language, such as C, C++, Cobol, Pascal, Java, Java-script, HTML, XML, dHTML, assembly or machine code programming, RTL, etc.

It is to be understood that the above description is intended to be illustrative and not restrictive. It readily should be apparent to one skilled in the art that various modifications may be made to the invention disclosed in this application without departing from the scope and spirit of the invention. The scope of the invention should, therefore, be determined not with reference to the above description, but should instead be determined with reference to the appended claims, along with the full scope of equivalents to which such claims are entitled. Throughout the disclosure various references, patents, patent applications, and publications are cited. Unless otherwise indicated, each is hereby incorporated by reference in its entirety for all purposes. All publications mentioned herein are cited for the purpose of describing and disclosing reagents, methodologies and concepts that may be used in connection with the present invention. Nothing herein is to be construed as an admission that these references are prior art in relation to the inventions described herein.

What is claimed is:

1. A computer system comprising:
a machine-readable medium,
an image sensor comprising a plurality of pixels in a two-dimensional spatial arrangement,
a primary analysis coprocessor card,
a first primary analysis coprocessor having a plurality of I/O ports,
a buffer, and
a plurality of second processors, wherein
the machine-readable medium encodes programming instructions that comprise instructions for:
obtaining from the image sensor, as part of a sequencing sample acquisition, a stream of serialized sensor data, wherein the serialized sensor data comprises frame-by-frame intensity values for the plurality of pixels of the image sensor representing optical measurements for sequencing emitted from a plurality of reaction cells of a removable integrated sequencing chip over a plurality of frames, wherein each reaction cell in the plurality of reaction cells corresponds to a single molecular experiment;
directly and continually inputting the stream of serialized sensor data at a rate of at least 100 frames per second into the primary analysis coprocessor card, wherein each frame is ordered in accordance with the two-dimensional spatial arrangement;
using the primary analysis coprocessor card to convert the stream of serialized sensor data into a format that can be input directly into the plurality of I/O ports of the first primary analysis coprocessor;
inputting the formatted stream of serialized sensor data directly into the-plurality of I/O ports of the first primary analysis coprocessor;
using the first primary analysis coprocessor to transpose the frame-by-frame intensity values of the formatted stream of serialized sensor data from the two-dimensional spatial arrangement into a corresponding plurality of reaction cell chunks, each respective reaction cell chunk in the corresponding plurality of reaction cell chunks representing movie data of a corresponding plurality of pixel intensity values, arranged in contiguous memory locations, of a corresponding reaction cell across the plurality of frames over a first predetermined time window;

storing the corresponding plurality of reaction cell chunks in contiguous memory locations within the buffer over a second predetermined time window to create a plurality of larger reaction cells chunks;

sending the plurality of larger reaction cell chunks from the buffer to the plurality of second processors;

using, with at least some single instruction multiple data (SIMD) instructions or multiple instruction multiple data (MIMD) instructions a plurality of logical cores of the plurality of second processors to convert, in each logical core in the plurality of logical cores, in parallel, the pixel intensity values into base-by-base sequence data concurrent with additional reaction cell chunks being received by the buffer from the first primary analysis coprocessor, causing the plurality of second processors to begin raw base calling before all the sensor data for the sequencing sample acquisition is obtained by the computer system.

2. The computer system of claim 1, wherein the primary analysis coprocessor card is configured with a cable connector that mates with a first serial cable that transfers the serialized sensor data.

3. The computer system of claim 2, configured as an instrument control server and a primary analysis server, wherein
the instrument control server includes:
the removable integrated sequencing chip, wherein the removable integrated sequencing chip comprises a first plurality of contacts;
an instrument control coprocessor card; and
a socket comprising a second plurality of contacts, wherein each respective contact in the second plurality of contacts is mated with a corresponding contact in the first plurality of contacts thereby exposing the socket to an analog stream of raw pixel data output from the integrated removable sequencing chip; and wherein
the instrument control coprocessor card is electronically coupled to the socket thereby causing the instrument control processor card to receive the analog stream of raw pixel data output from the socket; and wherein
the primary analysis server includes the primary analysis coprocessor card, the first primary analysis coprocessor, the buffer, and the plurality of second processors; and wherein the primary analysis coprocessor card is coupled to the first serial cable and receives the serialized sensor data from the primary analysis coprocessor card through the first serial cable.

4. The computer system of claim 3, further comprising: an acquisition simulator server including a simulation coprocessor card that is configured with a cable connector that mates with a second serial cable connected to the instrument control server for inputting simulated data/frames to the instrument control server without the need for the removable integrated sequencing chip.

5. The computer system of claim 2, wherein the first serial cable comprises at least one of: a coaxial cable, a twisted pair copper wire, an optical fiber, and an Ethernet cable.

6. The computer system of claim 2, wherein the first primary analysis coprocessor comprises a field programmable coprocessor.

7. The computer system of claim 6, wherein the instructions for using the first primary analysis coprocessor to transpose instruct the field programmable coprocessor to transpose the frame-by-frame intensity values to create the corresponding plurality of reaction cell chunks, while the plurality of second processors perform the raw base calling.

8. The computer system of claim 1, wherein the corresponding plurality of reaction cell chunks each represent movie data of the intensity values of a set of n pixels of the image sensor that are assigned to detect the intensity values emitted by the corresponding reaction cell, wherein n is at least one pixel, at least two pixels, at least three pixels, or at least four pixels.

9. The computer system of claim 8, wherein each of the reaction cells have at least two pixels assigned to detect the intensity values emitted by the corresponding reaction cell.

10. The computer system of claim 8, wherein the intensity values of the pixels for each of the corresponding plurality of reaction cell chunks are stored in contiguous memory locations.

11. The computer system of claim 8, wherein the first predetermined time window comprises 5-50 seconds, resulting in reaction cell chunks that are approximately 5-50 seconds in length.

12. The computer system of claim 8, wherein the second predetermined time window comprises 120-160 seconds, resulting in super reaction cell chunks that are approximately 120-160 seconds in length.

13. The computer system of claim 1, wherein the machine-readable medium further encodes programming instructions that:
partition the buffer into a set of tiles, such that as the data tiles are filled with reaction cell chunks, the data tiles are passed in order by the programming instructions encoded by the machine-readable medium to the plurality of second processors as the second processors become available; and
when a respective data tile is freed up, use the respective data tile to store additional reaction cell chunks, thereby making the computer system more tolerant of downstream processing delays in the plurality of second processors.

14. The computer system of claim 1, wherein the plurality of logical cores includes C logical cores, and each of the logical cores utilizes a SIMD register having N slots, wherein each slot processes an independent sequencing reaction for a respective reaction cell in the plurality of reaction cells, such that a total number of independent reactions E processed simultaneously for the C multiple cores is: $E = C \times N$.

15. The computer system of claim 1, wherein a second processor in the plurality of second processors supports SIMD instructions.

16. The computer system of claim 1, wherein a second processor in the plurality of second processors supports SIMD instructions to convert, in each logical core in the plurality of logical cores, in parallel, the pixel intensity values into base-by-base sequence data, and wherein the SIMD instructions are part of an AVX instruction set.

17. The computer system of claim 1, wherein a second processor in the plurality of second processors supports SIMD instructions to convert, in each logical core in the plurality of logical cores, in parallel, the pixel intensity values into base-by-base sequence data, and wherein the SIMD instructions are part of a VIS, MMX, SSE, or Altivec instruction set.

18. The computer system of claim 1, wherein the primary analysis coprocessor card and the first primary analysis coprocessor are functionally connected to a primary analysis coprocessor printed circuit board by a plurality of bus connectors.

19. The computer system of claim 1, wherein the instructions for directly and continually inputting the stream of serialized sensor data into the primary analysis coprocessor card directly and continually input the stream of serialized sensor data into the primary analysis coprocessor card at a rate of at least 450 megabytes per second.

20. The computer system of claim 1, wherein the machine-readable medium further encodes programming instructions that use the first primary analysis coprocessor to perform dark frame correction, with a dark frame acquired from the image sensor in the absence of light, and gain correction on the frame-by-frame intensity values of the formatted stream of serialized sensor data prior to forming the corresponding plurality of reaction cell chunks.

21. The computer system of claim 1, wherein the machine-readable medium further encodes programming instructions that:
   use the first primary analysis coprocessor to send reaction cell chunks in the plurality of reaction cell chunks on a repetitive basis over time to the buffer, thereby causing the buffer to receive multiple reaction cell chunks for each reaction cell in the plurality of reaction cells; and use the buffer, for each respective reaction cell in the plurality of reaction cells, to store reaction cell chunks, received from the primary analysis coprocessor, that are for the respective reaction cell and that are received over time from the primary analysis coprocessor buffer, in a corresponding set of contiguous memory locations for the respective reaction cell within the buffer, in order to create the plurality of larger reaction cell chunks, each respective larger reaction cell chunk in the plurality of larger reaction cells chunks comprising a corresponding plurality of reaction cell chunks for a corresponding reaction cell in the plurality of reaction cells.

* * * * *